US010071978B2

(12) United States Patent
Wesson et al.

(10) Patent No.: US 10,071,978 B2
(45) Date of Patent: *Sep. 11, 2018

(54) PROCESS FOR THE PRODUCTION OF ALPHA-TOCOTRIENOL AND DERIVATIVES

(71) Applicant: BioElectron Technology Corporation, Mountain View, CA (US)

(72) Inventors: Kieron W. Wesson, Burlingame, CA (US); Andrew W. Hinman, San Francisco, CA (US); Orion D. Jankowski, Burlingame, CA (US)

(73) Assignee: BIOELECTRON TECHNOLOGY CORPORATION, Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/068,452

(22) Filed: Mar. 11, 2016

(65) Prior Publication Data
US 2017/0037023 A1 Feb. 9, 2017

Related U.S. Application Data

(63) Continuation of application No. 14/038,675, filed on Sep. 26, 2013, now abandoned, which is a continuation of application No. 13/358,451, filed on Jan. 25, 2012, now Pat. No. 8,575,369, which is a continuation of application No. 12/606,923, filed on Oct. 27, 2009, now Pat. No. 8,106,223.

(60) Provisional application No. 61/197,585, filed on Oct. 28, 2008.

(51) Int. Cl.
C07D 311/72 (2006.01)
C07C 46/02 (2006.01)

(52) U.S. Cl.
CPC ............ *C07D 311/72* (2013.01); *C07C 46/02* (2013.01)

(58) Field of Classification Search
CPC .............................. C07D 311/72; C07C 46/02
See application file for complete search history.

(56) References Cited

U.S. PATENT DOCUMENTS

| 2,519,863 | A | 8/1950 | Weisler |
|---|---|---|---|
| 4,603,142 | A | 7/1986 | Burger et al. |
| 4,977,282 | A | 12/1990 | Baldwin et al. |
| 5,157,132 | A | 10/1992 | Tan et al. |
| 5,190,618 | A | 3/1993 | Top et al. |
| 5,660,691 | A | 8/1997 | Barnicki et al. |
| 5,932,748 | A | 8/1999 | Breuninger |
| 6,066,731 | A | 5/2000 | Müller et al. |
| 6,224,717 | B1 | 5/2001 | Sumner, Jr. et al. |
| 6,239,171 | B1 | 5/2001 | Lane et al. |
| 6,252,071 | B1 | 6/2001 | Müller et al. |
| 6,359,132 | B1 | 3/2002 | Müller et al. |
| 6,395,915 | B1 | 5/2002 | Bellafiore et al. |
| 6,562,372 | B1 | 5/2003 | Yokoi et al. |
| 6,590,113 | B1 | 7/2003 | Sleeter |
| 6,656,358 | B2 | 12/2003 | May et al. |
| 6,838,104 | B2 | 1/2005 | Jacobs |
| 6,977,270 | B2 | 12/2005 | Baldenius et al. |
| 7,034,054 | B2 | 4/2006 | Miller et al. |
| 7,038,067 | B2 | 5/2006 | Couladouros et al. |
| 7,432,305 | B2 | 10/2008 | Miller et al. |
| 7,470,798 | B2 | 12/2008 | Wang et al. |
| 7,491,312 | B2 | 2/2009 | Gilat et al. |
| 7,514,461 | B2 | 4/2009 | Wang et al. |
| 7,968,746 | B2 | 6/2011 | Jankowski et al. |
| 8,106,223 | B2 * | 1/2012 | Wesson ................ C07D 311/72 549/412 |
| 8,314,153 | B2 | 11/2012 | Miller et al. |
| 8,575,369 | B2 * | 11/2013 | Wesson ................ C07D 311/72 549/412 |
| 8,716,486 | B2 | 5/2014 | Hinman et al. |
| 8,716,527 | B2 | 5/2014 | Hinman et al. |
| 8,952,071 | B2 | 2/2015 | Hinman et al. |
| 9,162,957 | B2 | 10/2015 | Mollard |
| 9,278,085 | B2 | 3/2016 | Miller et al. |
| 9,296,712 | B2 | 3/2016 | Hinman et al. |
| 9,370,496 | B2 | 6/2016 | Miller |
| 2004/0116715 | A1 | 6/2004 | Baldenius et al. |
| 2004/0158083 | A1 | 8/2004 | Yuen May et al. |
| 2005/0124687 | A1 | 6/2005 | Couladouros et al. |
| 2006/0281809 | A1 | 12/2006 | Miller et al. |
| 2007/0238886 | A1 | 10/2007 | Ho |
| 2009/0076278 | A1 | 3/2009 | Dan-Oh et al. |
| 2011/0207828 | A1 | 8/2011 | Miller et al. |
| 2011/0269776 | A1 | 11/2011 | Miller |
| 2013/0109759 | A1 | 5/2013 | Miller |

(Continued)

FOREIGN PATENT DOCUMENTS

JP 63063674 A 3/1988
JP 1233278 A 9/1989

(Continued)

OTHER PUBLICATIONS

Written Opinion dated Dec. 23, 2009, for PCT Patent Application No. PCT/US09/62212, filed on Oct. 27, 2009, 6 pages.
Bertalan et al., "Recovery of fatty oil from theTransylvanian black current by means of supercritical and conventional extraction", Olaj, Szappn, Kozmetika, 2000, vol. 49 (Kulonszarriy), pp. 40-45; with English translation 14 pages.
Borch, R. F.,"Cyanohydridoborate anion as a selective reducing agent," Journal of the American Chemical Society 93,12 (1971): pp. 2897-2904.
Cheremisinoff, N. P., Liquid filtration. Butterworth-Heinemann, 1998, pp. 1-18.
Gu et al., "5-Trideuteromethyl-α-tocotrienol and 5-$^{14}CH_3$-α-tocotrienol as biological tracers of tocotrienols", *Journal of Labelled Compounds and Radiopharmaceuticals*, 2006, vol. 49, pp. 733-743.

(Continued)

Primary Examiner — John M Mauro
(74) Attorney, Agent, or Firm — Squire Patton Boggs (US) LLP

(57) ABSTRACT

The invention discloses novel processes for production, enrichment and/or isolation of alpha-tocotrienol from source material comprising at least one non-alpha-tocotrienol, such as natural extracts comprising mixed tocotrienols.

16 Claims, 4 Drawing Sheets

(56) References Cited

U.S. PATENT DOCUMENTS

| | | |
|---|---|---|
| 2013/0267538 A1 | 10/2013 | Walkinshaw et al. |
| 2013/0345312 A1 | 12/2013 | Jankowski et al. |
| 2014/0031433 A1 | 1/2014 | Miller et al. |
| 2014/0243424 A1 | 8/2014 | Mollard et al. |
| 2014/0249160 A1 | 9/2014 | Miller et al. |
| 2014/0275045 A1 | 9/2014 | Hinman et al. |
| 2014/0343166 A1 | 11/2014 | Miller et al. |
| 2015/0057363 A1 | 2/2015 | Miller et al. |
| 2015/0216820 A1 | 8/2015 | Miller et al. |
| 2015/0218079 A1 | 8/2015 | Shrader et al. |
| 2015/0297551 A1 | 10/2015 | Hinman et al. |
| 2016/0024085 A1 | 1/2016 | Hinman et al. |
| 2016/0039775 A1 | 2/2016 | Hinman et al. |
| 2016/0039776 A1 | 2/2016 | Hinman et al. |
| 2016/0115141 A1 | 4/2016 | Hinman et al. |

FOREIGN PATENT DOCUMENTS

| | | |
|---|---|---|
| JP | 2003-2777 | 1/2003 |
| JP | 2003-171376 | 6/2003 |
| JP | 2004-175805 | 6/2004 |
| WO | WO 99/38860 | 8/1999 |
| WO | WO 2002/050054 A2 | 6/2002 |
| WO | WO 2007/105336 A1 | 9/2007 |
| WO | WO 2008/142433 A1 | 11/2008 |

OTHER PUBLICATIONS

International Search Report dated Dec. 23, 2009, for PCT Patent Application No. PCT/US09/62212, filed on Oct. 27, 2009, 2 pages.

Kabbe et al., "A new synthesis of 3,4-dehydro-a-tocotrienol and vitamin E", *Synthesis*, 1978, vol. 12, pp. 888-889. (Translation of Abstract only: Chemical Abstract CAPLUS No. 1979:168774, 2 pages.).

Kajiwara et al., "Studies on Tocopherols 111. Convenient Synthesis of Tocopherols," Heterocycles, 1980, vol. 14, No. 12, pp. 1995-1998.

Maeda, Y. et al. (Dec. 16, 1994). "Rearrangement of (Polymethoxybenzyl) Ammonium N-Methylides," J. Org. Chem. 59(25):7897-7901.

Mayer, H. et al. (1967). "Ober die Chemie des Vitamins E. 8. Mitteilung [1]. Die Stereochemie von natulichem y-Tocotrienol (Plastochromanol-3), Plastochromanol-8 and Plastochromenol-81)," Helvetica Chimica Acta 50(5):1376-1393. (Translation of Abstract Only: Chemical Abstracts CAPLUS Abstract No. 1967:473698. 1 page, and publisher's document Web page description, 2 pages.).

Netscher et al. (2007). "Tocopherols by Hydride Reduction of Dialkylamino Derivatives," European Journal of Organic Chemistry, pp. 1176-1183.

Netscher et al. (Sep. 2001). "Aminomethylation of Vitamin E Compounds," located at <http://www.mdpi.net/ecsoc/ecsoc-5/Papers/c0007/c0007.htm», last visited on Oct. 21, 2008, 4 pages.

Ogawa et al., "y-Tocopheryl Quinone, Not A-Tocopheryl Quinone, Induces Adaptive Response Through Up-Regulation of Cellular Glutathione and Cysteine Availability Via Activation of ATF4", *Free Radical Research*, Jul. 2008, vol. 42, No. 7, pp. 674-687.

Pearce et al., "Inhibitors of Cholesterol Biosynthesis. 2. Hypocholesterolemic and Antioxidant Activities of Ben zopyran and Tetrahydronaphthalene Analogues of the Toeotrienols", *J. Med. Chem.*, 1994, vol. 37, pp. 526-541.

Pearce et al. "Hypocholesterolemic Activity of Synthetic and Natural Tocotrienols", *J. Med. Chem.*, 1992, vol. 35, pp. 3595-3606.

Schudel et al., "Uber die Chemie des Vitamins E. 5. Mitteilung. Die Synthese von rac. all-trans-$\xi_1$-and-$\epsilon$-Tocopherol," *Helvetica Chimica Acta*, 1963, vol. XLVI, Fasc. 7, No. 281, pp. 2517-2526. (English summary on p. 2526.).

Scott et al., "Syntheses of (2R,4'R,8'R)-α-Tocopherol and (2R,3'E,7'E)-α-Tocotrienol," *Helvetica Chimica Acta*, 1976, vol. 59, Fasc. 1, pp. 290-306, Nr. 34-35.

Strohschein et al., "Separation and Identification of Tocotrienol Isomers by HPLC-MS and HPLC-NMR Coupling," Anal Chem, 1999, vol. 71, pp. 1780-1785.

Tayama et al. (2006). "Asymmetric [1,2] Stevens Rearrangement of (S)-N-Benzylic Proline-Derived Ammonium Salts under Biphasic Conditions," Chemistry Letters 35(5):478-479.

Urano et al., "Synthesis of dl-α-Tocopherol and dl-α-Tocotrienol", *Chem. Pharm. Bull.*, 1983, vol. 31, pp. 4341-4345.

Wu et al. (2007). "Preparation of High Content d-a-tocopherol," China Oils and Fats (Zhongguo Youzhi) 32(6):55-57. (English abstract only).

\* cited by examiner

PROCESS FOR THE PRODUCTION OF ALPHA-TOCOTRIENOL AND DERIVATIVES

CROSS-REFERENCE TO RELATED APPLICATIONS

This application claims priority benefit of U.S. provisional patent application No. 61/197,585, filed Oct. 28, 2008. The content of that application is incorporated herein by reference in its entirety.

TECHNICAL FIELD

This invention relates generally to a process for production, enrichment and/or isolation of pure alpha-tocotrienol from natural extracts that comprise mixed tocols. In particular, the invention relates to a novel and effective process for production, enrichment and/or isolation of alpha-tocotrienol of high purity from plant extracts, e.g. palm oil extract such as Tocomin®, that is economically feasible on a commercial scale. The invention also relates to a process for the synthesis of alpha-tocotrienol quinone of high purity. The invention also relates to the alpha-tocotrienol-containing product produced by the process.

BACKGROUND OF THE INVENTION

The present invention provides a process for the production, enrichment and/or isolation of pure alpha-tocotrienol enriched tocotrienol compositions from naturally occurring extracts, and to the alpha-tocotrienol-containing product produced by the process. This process can be performed without chromatography, or with minimal use of chromatography, and is economically feasible on a commercial scale.

Tocopherols and tocotrienols are molecules characterized by a 6-chromanol ring structure and a side chain at the C-2-position. Tocotrienols possess a 4', 8', 12' trimethyltridecyl unsaturated phytol side chain with the presence of double bonds at 3', 7', and 11' positions of the side chain, while tocopherols have a saturated side chain. The geometry of each of these double bond sites is trans (also referred to as E) in all four natural tocotrienols. There are four naturally occurring tocotrienols, d-alpha-, d-beta-, d-gamma-, and d-delta-tocotrienol. The four naturally occurring tocotrienols have the (R) absolute configuration at the C-2 chroman ring position.

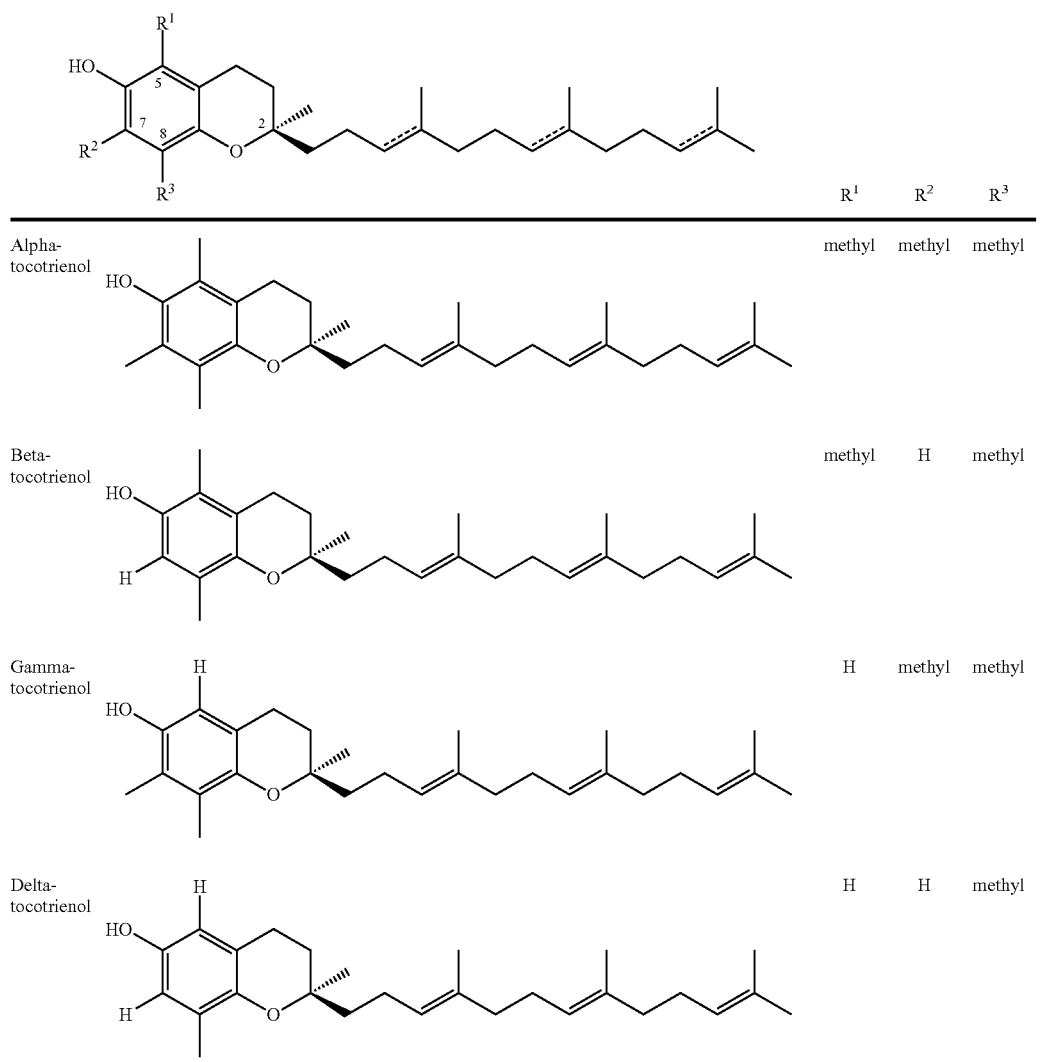

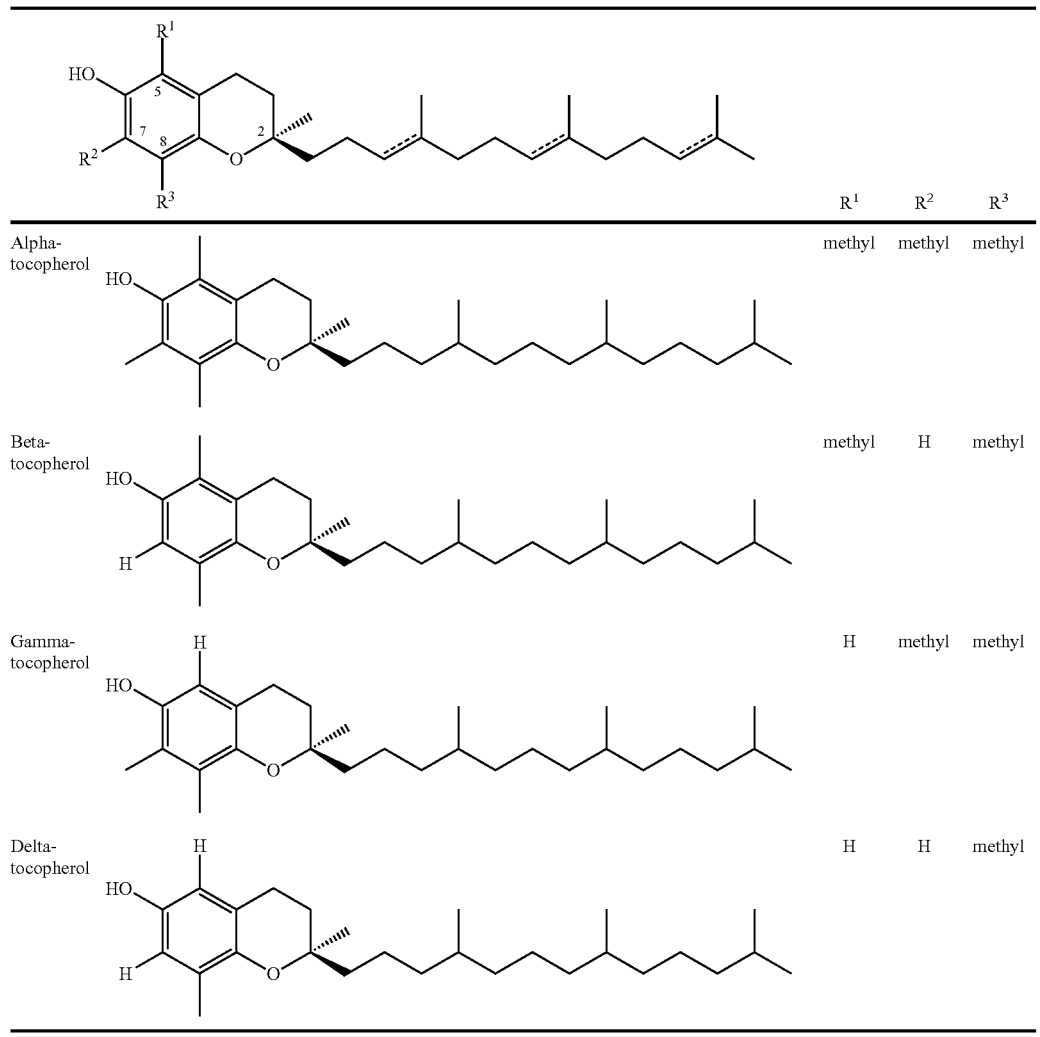

Tocotrienols are present in the oils, seeds, and other parts of many plants used as foods (see pp. 99-165 in L. Machlin, ed., "Vitamin E: A Comprehensive Treatise" for a discussion of the occurrence of tocotrienols in foods). Tocotrienol-containing concentrates can be prepared from certain plant oils and plant oil by-products such as rice bran oil or palm oil distillate. For examples of such isolation processes, see for instance A. G. Top et al., U.S. Pat. No. 5,190,618 (1993) or Tanaka, Y. et al., Japanese Patent No. JP2003-171376 (2003).

There is a problem inherent in obtaining tocotrienols from natural sources, in that the tocotrienol yield from such processes is a mixture of varying amounts of all of the natural tocotrienols and tocopherols. In order to obtain a pure member of the tocotrienol family, it has been necessary to resort to very expensive procedures such as preparative scale reverse-phase chromatography or simulated moving bed chromatography. For an example of such a purification process, see M. Kitano et al., Japanese Patent No. 2003-02777 (2003) or Burger et al., U.S. Pat. No. 4,603,142.

The synthesis of tocotrienols in the natural form, having the (2R) chiral configuration and trans double bonding at the proper locations in the side chain, has also been proven to be of considerable difficulty.

Syntheses of various members of the tocotrienol family in the d,l- or (RS)-form have been published; see for example Schudel et al., Helv. Chim. Acta (1963) 46, 2517 2526; H. Mayer et al., Helv. Chim. Acta (1967) 50, 1376 11393; H.-J. Kabbe et al., Synthesis (1978), 888 889; M. Kajiwara et al., Heterocycles (1980) 14, 1995 1998; S. Urano et al., Chem. Pharm. Bull. (1983) 31, 4341 4345, Pearce et al., J. Med Chem. (1992), 35, 3595 3606 and Pearce et al., J. Med Chem. (1994). 37, 526 541. None of these reported processes lead to the natural form of the tocotrienols, but rather produce racemic mixtures. Syntheses of natural form d-tocotrienols have been published. See for example, J. Scott et al., Helv. Chim. Acta (1976) 59, 290 306, Sato et al. (Japanese Patent 63063674); Sato et al. (Japanese Patent No. JP 01233278) and Couladouros et al (U.S. Pat. No. 7,038, 067).

Tocotrienols occur largely in palm oil, rice bran oil, and barley. While synthetic and natural tocopherols are readily available in the market, the supply of natural tocotrienols is limited, and generally comprises a mixture of tocotrienols. Crude palm oil which is rich in tocotrienols (800-1500 ppm) offers a potential source of natural tocotrienols. Carotech, located in Malaysia, is an industrial plant able to extract and concentrate tocotrienols from crude palm oil. Carotech uses a molecular distillation process (employing ultra-high vacuum and very low temperature) in its production plant. This process (see U.S. Pat. No. 5,157,132) allows Carotech to extract phytonutrients such as the Tocotrienol Complex (Tocomin®, a registered trademark of Carotech for extracts and concentrates of palm tree fruits) from the crude palm oil. Tocomin®-50 typically comprises about 25.32% mixed tocotrienols (7.00% alpha-tocotrienol, 14.42% gamma tocotrienol, 3.30% delta tocotrienol and 0.6% beta tocotrienol), 6.90% alpha-tocopherol and other phytonutrients such as plant squalene, phytosterols, co-enzyme Q10 and mixed carotenoids.

Additional commercially available products that may be used in the present invention are for example, Nu Triene Tocotrienol® (30% content, a product of Eastman Chemical Company), various Oryza® tocotrienol products of different tocotrienol concentrations from Oryza Oil & Fat Co. Ltd including Oryza tocotrienol-70 with 70% total tocopherol/tocotrienol content, and a total tocotrienol content of 40% including 14% of alpha-tocotrienol and 24% gamma-tocotrienol, and Oryza tocotrienol-90 with 90% total tocopherol/tocotrienol content and a total tocotrienol content of 60%; Golden Hope Plantations Berhad Tocotrienol oil (70% content), Davos Life Science TRF (63% content), Ginnoway™ tocotrienol concentrate from palm and rice oil from Beijing Gingko Group, Gold Trie® a product of Sime Darby Biorganic Sdn Bhd and Palm Nutraceuticals Sdn Bhd (89% content). Delta Tocotrienol-92® (92% pure by HPLC) is a commercially available product from Beijing Gingko Group that may be also used in the present invention.

Methods for isolation or enrichment of tocotrienol from certain plant oils and plant oil by-products have been described in the literature, but these methods generally produce mixtures of natural tocols in varying amounts and are not economically feasible on a commercial scale. As mentioned above, in order to obtain a pure member of the tocotrienol family, it has been necessary to resort to expensive procedures such as preparative scale reversed-phase chromatography or simulated moving bed chromatography. For some examples of such isolation and purification processes, see for instance Top A. G. et. al., U.S. Pat. No. 5,190,618; Lane R et al., U.S. Pat. No. 6,239,171; Bellafiore, L. et al U.S. Pat. No. 6,395,915; May, C. Y et al., U.S. Pat. No. 6,656,358; Jacobs, L et al, U.S. Pat. No. 6,838,104; Sumner, C et al. Int. Pat. Pub. WO 99/38860, or Jacobs, L. Int. Pat. Pub. WO 02/500054.

Production of d-alpha tocopherol from natural plant sources has been described in U.S. Pat. No. 4,977,282, where natural plant sources having Vitamin E activity of a concentrate of mixed tocopherols that might include tocotrienols are transformed into alpha-tocopherol. In this isolation, alpha tocopherol is enriched after amino-alkylating the mixed tocopherols which are then reduced by catalytic hydrogenation to convert the mixture of the non-alpha tocopherol tocols into alpha-tocopherol. In this process, any tocotrienols present would be hydrogenated to tocopherol. See Netscher et al. (2007) *Eur J. Org. Chem* 1176-1183

Because of the similar molecular and retention characteristics of the various individual tocopherols and tocotrienols, separation of the individual compounds has been proven difficult and not commercially viable. Although the process for the production of alpha-tocotrienol has been described, it is only available in pure form at very high prices (e.g., USD$672 for 100 mg of ≥98% pure alpha-tocotrienol from Fluka Chemical Company in October, 2009).

In light of the above, there remains a need for a method of producing the naturally occurring alpha-tocotrienol in a pure form that is economically feasible on a commercial scale. Such a process would minimize the number of processing steps required, and would not require, or would minimize the use of, chromatographic separations.

DISCLOSURE OF THE INVENTION

In accordance with the purposes of this invention, in one aspect, this invention relates to a novel process for the production, enrichment, and/or isolation of alpha-tocotrienol from source material comprising at least one tocotrienol which is not alpha-tocotrienol. In some embodiments, the at least one tocotrienol which is not alpha-tocotrienol comprises beta-tocotrienol, gamma-tocotrienol, or delta-tocotrienol; or any two of beta-tocotrienol, gamma-tocotrienol, or delta-tocotrienol; or all three of beta-tocotrienol, gamma-tocotrienol, and delta-tocotrienol. In any of the foregoing embodiments, the source material can optionally also comprise alpha tocopherol. In one embodiment, this invention relates to a novel process for the production, enrichment and/or isolation of pure alpha-tocotrienol from plant extracts comprising naturally occurring mixed tocotrienols. In one embodiment, this invention relates to a novel process for the production, enrichment and/or isolation of pure alpha-tocotrienol from plant extracts enriched in naturally occurring mixed tocotrienols. In one embodiment the invention does not need the use of chromatography, and is amenable to large commercial production of alpha-tocotrienol. In another embodiment the invention needs minimal use of chromatography and is amenable to large commercial production of alpha-tocotrienol In one embodiment, the invention relates to a novel process for the production, enrichment and/or isolation of pure alpha-tocotrienol from naturally occurring extracts comprising a mixture of tocotrienols and alpha tocopherol. In another embodiment, the naturally occurring extract is a palm oil extract, a palm fruit extract, or a palm oil/palm fruit extract. In another embodiment, the naturally occurring extract is a palm oil extract, a palm fruit extract, or a palm oil/palm fruit extract which has been concentrated. In another embodiment, the naturally occurring extract is a palm oil extract, a palm fruit extract, or a palm oil/palm fruit extract from *Elaeis guineensis*. In another embodiment, the naturally occurring extract is a palm oil extract a palm fruit extract, or a palm oil/palm fruit extract from *Elaeis guineensis* which has been concentrated. In another embodiment, the naturally occurring extract is the commercial palm oil concentrate Tocomin®, a product of Carotech Bhd. (Malaysia), which comprises a mixture of tocotrienols and alpha-tocopherol extracted and concentrated from virgin crude palm oil/palm fruits (*Elaeis guineensis*) and which also includes non-tocol phytonutrients such as plant squalene, phytosterols, co-enzyme Q10 and mixed carotenoids that are naturally extracted together with tocotrienols from palm fruits. In some embodiments, the naturally occurring extract is an extract of palm oil, rice bran oil, barley or annatto, or any combination of two or more of the foregoing oils. In another embodiment the formulation of the present invention comprises an enriched tocotrienol extract from palm oil, as sold by Carotech, Golden Hope Bioorganic, Davos Life Science, Beijing Gingko Group, Eisai, Eastman Corporation, Sime Darby Biorganic Sdn Bhd or Palm Nutraceuticals.

Another embodiment of the invention comprises the production, enrichment and/or isolation of natural d-alpha-tocotrienol from a material comprising at least one compound selected from:

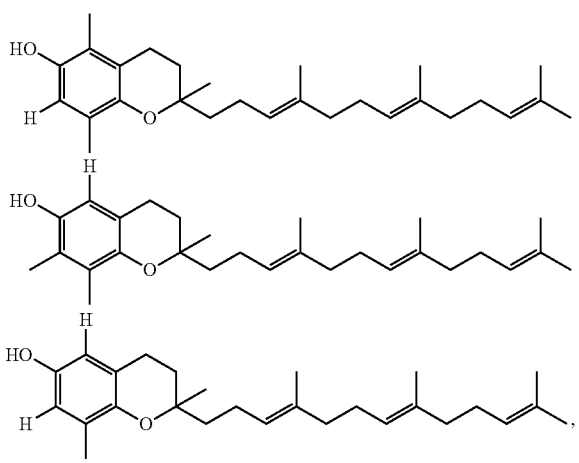

reacting said material with a formaldehyde equivalent and at least one amine compound of the formula H—N($R_{11}$)($R_{12}$), where $R_{11}$ and $R_{12}$ are independently selected from the group consisting of H and $C_1$-$C_8$ alkyl, or where $R_{11}$ and $R_{12}$ are combined together with the nitrogen to which they are bonded to form a five-to-eight membered heterocyclic ring, said heterocyclic ring having zero, one, or two additional heteroatoms in addition to the nitrogen to which $R_{11}$ and $R_{12}$ are bonded, to produce at least one aminomethylated compound selected from:

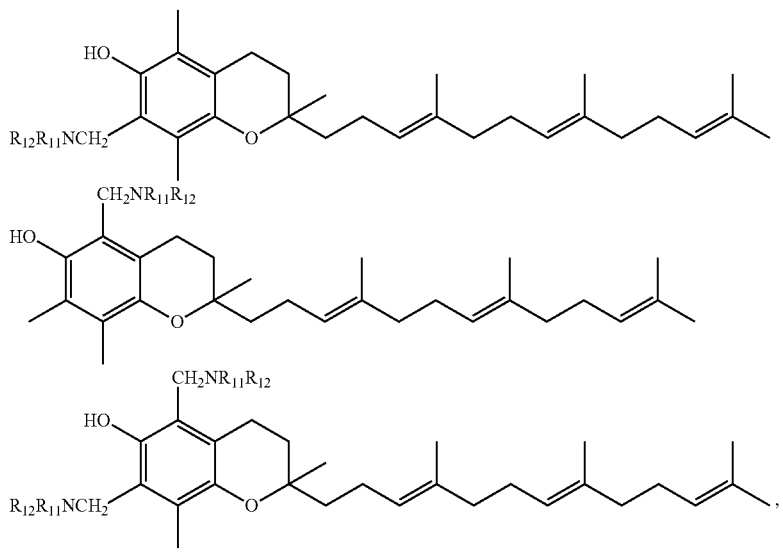

separating the aminomethylated compound or compounds from non-aminomethylated compounds, and reducing the aminomethylated compound or compounds to yield

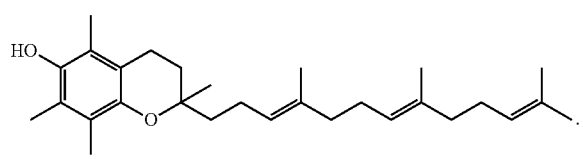 [SMILES: CC(C)=CCC/C(C)=C/CC/C(C)=C/CCC1(C)CCc2c(C)c(O)c(C)c(C)c2O1]

One embodiment of the invention, as described in FIG. 1, comprises the production, enrichment and/or isolation of natural d-alpha-tocotrienol from natural plant sources that comprise at least one non-alpha tocotrienol, and optionally additional tocotrienols, and that optionally also include alpha tocopherol and optionally other tocols and optionally non-tocol phytonutrients or impurities, comprising the steps of:

1a.) reacting a plant extract mixture with suitable reagents which will react with the one or more non-alpha-tocols to introduce a functional group in the free 5 and/or 7 positions of the one or more non-alpha-tocols;

1b.) separating the one or more non-alpha-tocols homologues that have been functionalized, from the alpha-tocotrienol, the optional alpha tocopherol and other non-tocol compounds that may be present;

1c.) optionally further separating the alpha-tocotrienol in the mixture separated in step (1b), from the optional alpha tocopherol and other non-tocol compounds;

1d.) chemically reacting the one or more non-alpha-tocol functionalized homologues from step (1b) to give alpha-tocotrienol; and 1e.) optionally combining the alpha-tocotrienol from step (1c) with the newly produced alpha-tocotrienol from step (1d) to give alpha-tocotrienol of high purity.

In another embodiment, step 1b) is followed by an optional step 1b1) of filtering a solution of the one or more non-alpha-tocols homologues that have been functionalized. Filtration can be performed using diatomaceous earth such as Celite® or any other method of filtration known to the skilled artisan.

In another embodiment, step 1d) is followed by an optional step 1d1), wherein a solution of the alpha-tocotrienol (in a solvent such as toluene) produced by the reduction is mixed with silica gel. The silica gel is removed by filtration, and the remaining filtrate is concentrated to give alpha-tocotrienol of high purity.

In another embodiment, both steps 1b1) and 1d1) are performed.

In another embodiment, the plant extract is a palm oil plant extract. In another embodiment, the plant extract is a palm fruit plant extract. In another embodiment, the plant extract is a rice extract. In another embodiment, the plant extract is a rice bran oil extract. In another embodiment, the plant extract is a barley extract. In another embodiment, the plant extract is an annatto extract. In another embodiment, the plant extract is a mixture of two or more of the foregoing plant extracts.

In one embodiment, introduction of a functional group in the free 5 and/or 7 positions of the non-alpha tocol homologues comprises introduction of a group which provides for increased differential solubility of the functionalized non-alpha tocol homologues compared to non-functionalized compounds in the starting material, source material, or extract. The increased differential solubility can be differential solubility in a single solvent, or increased differential solubility between two or more solvents in a mixed solvent system. In one embodiment, the introduction of a functional group in the free 5 and/or 7 positions of the non-alpha tocol homologues is accomplished without reducing the double bonds present in tocotrienol compounds and/or without causing isomerization of the double bonds present in tocotrienol compounds. In one embodiment, the step of chemically reacting the non-alpha tocol functionalized homologues to produce alpha-tocotrienol is accomplished without reducing the double bonds present in tocotrienol compounds and/or without causing isomerization of the double bonds present in tocotrienol compounds.

In one embodiment, the functionalization is introduced by amino-alkylation followed by acidification, thus converting the non-alpha-tocotrienol into the corresponding amino-alkylated product and converting said products to acid salts. In some embodiments, the functionalization is introduced by amino-alkylation with a formaldehyde equivalent, such as paraformaldehyde, and an amine, such as a secondary amine, such as a cyclic amine such as 1-methylpiperazine, piperidine or morpholine. In some embodiments, the functionalization is introduced by amino-alkylation with paraformaldehyde and 1-methylpiperazine. In some embodiments, the functionalization is introduced by amino-alkylation with paraformaldehyde and morpholine.

In one embodiment, the separation of the amino-alkylation products from the alpha-tocotrienol, the optional alpha tocopherol and other non-tocol compounds that may be present is done by partitioning between two organic layers. In one embodiment, the separation of the amino-alkylation products from the alpha-tocotrienol, the optional alpha tocopherol and other non-tocol compounds that may be present is done by partitioning between an organic layer and an aqueous layer. In one embodiment, the separation of the amino-alkylation products from the alpha-tocotrienol, the optional alpha tocopherol and other non-tocol compounds that may be present is done by partitioning using an acidic organic layer such as acetonitrile comprising formic acid.

In another embodiment, the non-alpha-tocotrienol functionalized homologues are reduced with a hydride reagent such as sodium cyano borohydride ($NaCNBH_3$). In another embodiment, the non-alpha-tocotrienol functionalized homologues are reduced with a hydride reagent such as sodium borohydride. In another embodiment, the non-alpha-tocotrienol functionalized homologues are reduced with lithium borohydride, zinc borohydride, or tetraalkylammonium hydride. In yet another embodiment, the non-alpha-tocotrienol functionalized homologues are reduced with a hydride reagent such as lithium aluminum hydride. In yet another embodiment, the non-alpha-tocotrienol functionalized homologues are reduced with a borane, diborane, or a borane complex, such as borane-t-butyl amine complex. In another embodiment, the non-alpha-tocotrienol functionalized homologues are reduced electrochemically or with an electron donor such as sodium, lithium, magnesium, potassium, zinc, nickel, or amalgams thereof, in the presence of a suitable proton source such as ammonium salts or carboxylic acids.

In any of the embodiments above, the processes of the invention can yield alpha-tocotrienol of high purity. In some embodiments, the purity is in the range of 80% to 99.9%, or in the range of 85% to 99.9%, or in the range of 90% to 99.9%, or in the range of 95% to 99.9%. In some embodiments, the purity is in the range of about 80% to about 99.9%, or in the range of about 85% to about 99.9%, or in the range of about 90% to about 99.9%, or in the range of about 95% to about 99.9%. In some embodiments, the purity is more than 80%, or more than 85%, or more than 90%, or more than 91%, or more than 92%, or more than 93%, or more than 94%, or more than 95%, or more than 96%, or more than 97%, or more than 98%, or more than 99%, or more than 99.5%, or more than 99.9%. In some embodiments, the purity is more than about 80%, or more than about 85%, or more than about 90%, or more than about 91%, or more than about 92%, or more than about 93%, or more than about 94%, or more than about 95%, or more than about 96%, or more than about 97%, or more than about 98%, or more than about 99%, or more than about 99.5%, or more than about 99.9%. In other embodiments, the impurities in the final product are less than 20%, or less than 15%, or less than 10%, or less than 5%, or less than 4%, or less than 3%, or less than 2%, or less than 1%, or less than 0.5%, or less than 0.1%. In other embodiments, the impurities in the final product are less than about 20%, or less than about 15%, or less than about 10%, or less than about 5%, or less than about 4%, or less than about 3%, or less than about 2%, or less than about 1%, or less than about 0.5%, or less than about 0.1%. In other embodiments, the impurities consisting of tocols or tocol derivatives in the final product are less than 5%, less than 4%, less than 3%, less than 2%, less than 1%, less than 0.5% or less than 0.1%. In other embodiments, the impurities consisting of tocols or tocol derivatives in the final product are less than about 5%, less than about 4%, less than about 3%, less than about 2%, less than about 1%, less than about 0.5% or less than about 0.1%. In one embodiment, the invention provides a method for large-scale production, enrichment, and/or isolation of alpha-tocotrienol, such as quantities of material containing alpha-tocotrienol of at least 50 grams, at least 100 grams, at least 250 grams, at least 500 grams, at least 1 kilogram, at least 2 kilograms, at least 5 kilograms, or at least 10 kilograms, or at least about 50 grams, at least about 100 grams, at least about 250 grams, at least about 500 grams, at least about 1 kilogram, at least about 2 kilograms, at least about 5 kilograms, or at least about 10 kilograms. The quantity of material containing alpha-tocotrienol can have any purity level as recited herein.

In some of the above mentioned embodiments, the process involves an additional optional step, wherein the alpha-tocotrienol of high purity is oxidized to produce alpha-tocotrienol quinone of high purity. In one embodiment, the conversion of alpha-tocotrienol to alpha-tocotrienol quinone is carried out under buffered conditions. In one embodiment, the buffer and/or base employed during conversion of alpha-tocotrienol to alpha-tocotrienol quinone is sodium carbonate, sodium hydrogen carbonate, potassium carbonate, potassium hydrogen carbonate, phosphate buffer, or any mixture in any proportion of two or more of the foregoing buffers.

In any of the embodiments above, the processes of the invention can yield alpha-tocotrienol quinone of high purity. In some embodiments, the purity is in the range of 80% to 99.9%, or in the range of 85% to 99.9%, or in the range of 90% to 99.9%, or in the range of 95% to 99.9%. In some embodiments, the purity is in the range of about 80% to about 99.9%, or in the range of about 85% to about 99.9%, or in the range of about 90% to about 99.9%, or in the range of about 95% to about 99.9%. In some embodiments, the purity is more than 80%, or more than 85%, or more than 90%, or more than 91%, or more than 92%, or more than 93%, or more than 94%, or more than 95%, or more than 96%, or more than 97%, or more than 98%, or more than 99%, or more than 99.5%, or more than 99.9%. In some embodiments, the purity is more than about 80%, or more than about 85%, or more than about 90%, or more than about 91%, or more than about 92%, or more than about 93%, or more than about 94%, or more than about 95%, or more than about 96%, or more than about 97%, or more than about 98%, or more than about 99%, or more than about 99.5%, or more than about 09.9%. In other embodiments, the impurities in the final product are less than 20%, or less than 15%, or less than 10%, or less than 5%, or less than 4%, or less than 3%, or less than 2%, or less than 1%, or less than 0.5%, or less than 0.1%. In other embodiments, the impurities in the final product are less than about 20%, or less than about 15%, or less than about 10%, or less than about 5%, or less than about 4%, or less than about 3%, or less than about 2%, or less than about 1%, or less than about 0.5%, or less than about 0.1%. In other embodiments, the impurities consisting of tocols or tocol derivatives in the final product are less than 5%, less than 4%, less than 3%, less than 2%, less than 1%, less than 0.5% or less than 0.1%. In other embodiments, the impurities consisting of tocols or tocol derivatives in the final product are less than about 5%, less than about 4%, less than about 3%, less than about 2%, less than about 1%, less than about 0.5% or less than about 0.1%. In one embodiment, the invention provides a method for large-scale production, enrichment and/or isolation of alpha-tocotrienol quinone, such as quantities of material containing alpha-tocotrienol quinone of at least 50 grams, at least 100 grams, at least 250 grams, at least 500 grams, at least 1 kilogram, at least 2 kilograms, at least 5 kilograms, or at least 10 kilograms, or at least about 50 grams, at least about 100 grams, at least about 250 grams, at least about 500 grams, at least about 1 kilogram, at least about 2 kilograms, at least about 5 kilograms, or at least about 10 kilograms. The quantity of material containing alpha-tocotrienol quinone can have any purity level as recited herein.

In another embodiment, the invention comprises a method for oxidizing alpha-tocotrienol to alpha-tocotrienol quinone with minimal isomerization of the double bonds of the triene moiety. In some embodiments, the alpha-tocotrienol quinone, 2-((6E,10E)-3R-hydroxy-3,7,11,15-tetramethylhexadeca-6,10,14-trienyl)-3,5,6-trimethylcyclohexa-2,5-diene-1,4-dione, produced by the method comprises at least about 80%, at least about 90%, at least about 95%, at least about 96%, at least about 97%, at least about 98%, at least about 99%, at least about 99.5%, or at least about 99.9% of the 2-(3-hydroxy-3,7,11,15-tetramethylhexadeca-6,10,14-trienyl)-3,5,6-trimethylcyclohexa-2,5-diene-1,4-dione material present.

In any of the above embodiments, the oxidation of alpha-tocotrienol to alpha-tocotrienol quinone can be performed with cerium (IV) ammonium nitrate.

In another embodiment, a solution of alpha-tocotrienol quinone, in a solvent such as isopropylacetate, n-heptane, or a mixture of isopropylacetate and n-heptane, is placed on a chromatography column packed with silica gel. The silica gel can contain between about 0.1-5% by weight of sodium hydrogen carbonate, such as about 0.5-2% by weight or about 1% by weight of sodium hydrogen carbonate. The alpha-tocotrienol quinone can be eluted from the silica gel/NaHCO$_3$ with solvents, such as n-heptane, isopropylacetate, or n-heptane:isopropylacetate in ratios of about 100:1, about 100:5, about 100:10, or about 100:15. The recovered solution of alpha-tocotrienol quinone can be concentrated to give alpha-tocotrienol quinone of high purity.

In another embodiment the foregoing quantities of alpha-tocotrienol or alpha-tocotrienol quinone can be produced using a single performance of the method, that is, with a single iteration of the steps of the method.

One embodiment of the invention, as described in FIG. 2, comprises the production, enrichment and/or isolation of natural d-alpha-tocotrienol from a natural plant source extract from palm oil, wherein said extract composes at least one non-alpha tocotrienol, comprising the steps of:

2a.) reacting a palm oil extract mixture with aminoalkylating agents which will react with the one or more non-alpha-tocols to introduce a functional group in the free 5 and/or 7 positions of the one or more non-alpha-tocotrienols and converting the products into acid salts, 2b.) separating the one or more non-alpha-tocotrienol acid salts of the products from step (2a), from the alpha-tocotrienol, optional alpha tocopherol and other non-tocol compounds that may be present; and 2c.) reducing the non-alpha-tocotrienol functionalized homologues with a reducing agent to give alpha-tocotrienol of high purity.

In this particular embodiment, the alpha-tocotrienol separated from the one or more amino-alkyl tocotrienol homologues in step (2b) is not recovered, thus allowing for a process yielding pure alpha-tocotrienol without the need of intensive and/or expensive chromatography.

In another embodiment, the process does not comprise an additional step wherein the alpha-tocotrienol from step (2b) is recovered, thus allowing for a more economical commercial process.

In another embodiment, step 2b) is followed by an optional step 2b1) of filtering a solution of the one or more non-alpha-tocols homologues that have been functionalized. Filtration can be performed using diatomaceous earth such as Celite® or any other method of filtration known to the skilled artisan.

In another embodiment, step 2c) is followed by an optional step 2c1), wherein a solution of the alpha-tocotrienol (in a solvent such as toluene) produced by the reduction is mixed with silica gel. The silica gel is removed by filtration, and the remaining filtrate is concentrated to give alpha-tocotrienol of high purity.

In another embodiment, both step 2b1) and 2c1) are performed.

In one embodiment, the palm oil extract is commercially available Tocomin®. In another embodiments the palm oil extract is commercially available Tocomin®-50.

In one embodiment, introduction of an aminoalkyl group in the free 5 and/or 7 positions of the non-alpha tocol homologues provides for increased differential solubility of the functionalized non-alpha tocol homologues compared to non-functionalized compounds in the starting material, source material, or extract. The increased differential solubility can be differential solubility in a single solvent, or increased differential solubility between two or more solvents in a mixed solvent system. In one embodiment, the introduction of an aminoalkyl group in the free 5 and/or 7 positions of the non-alpha tocol homologues is accomplished without reducing the double bonds present in tocotrienol compounds and/or without causing isomerization of the double bonds present in tocotrienol compounds. In one embodiment, the step of reducing the non-alpha tocol functionalized homologues to produce alpha-tocotrienol is accomplished without reducing the double bonds present in tocotrienol compounds and/or without causing isomerization of the double bonds present in tocotrienol compounds.

In another embodiment, the amino-alkylation is performed with a formaldehyde equivalent, such as paraformaldehyde, and an amine, such as a secondary amine, such as a cyclic amine selected from 1-methylpiperazine, piperidine or morpholine. In yet another embodiment the amino-alkylation is performed with paraformaldehyde and 1-methylpiperazine. In yet another embodiment, the amino-alkylation is performed with paraformaldehyde and morpholine.

In another embodiment, the reduction is performed with a hydride reagent such as lithium aluminum hydride, lithium borohydride, zinc borohydride, tetraalkylammonium hydride, sodium borohydride or sodium cyano borohydride.

In another embodiment, the reduction is performed with a borane, diborane, or a borane complex, such as borane t-butyl amine complex.

In another embodiment, the reduction is performed electrochemically or with an electron donor such as sodium, lithium, potassium, magnesium, zinc or nickel or amalgams thereof in the presence of a suitable proton source, such as a protic solvent such as an organic alcohol or liquid ammonia, or such as ammonium salts or carboxylic acids.

In any of the embodiments above, the processes of the invention can yield alpha-tocotrienol of high purity. In some embodiments, the purity is in the range of 80% to 99.9%, or in the range of 85% to 99.9%, or in the range of 90% to 99.9%, or in the range of 95% to 99.9%. In some embodiments, the purity is in the range of about 80% to about 99.9%, or in the range of about 85% to about 99.9%, or in the range of about 90% to about 99.9%, or in the range of about 95% to about 99.9%. In some embodiments, the purity is more than 80%, or more than 85%, or more than 90%, or more than 91%, or more than 92%, or more than 93%, or more than 94%, or more than 95%, or more than 96%, or more than 97%, or more than 98%, or more than 99%, or more than 99.5%, or more than 99.9%. In some embodiments, the purity is more than about 80%, or more than about 85%, or more than about 90%, or more than about 91%, or more than about 92%, or more than about 93%, or more than about 94%, or more than about 95%, or more than about 96%, or more than about 97%, or more than about 98%, or more than about 99%, or more than about 99.5%, or more than about 99.9%. In other embodiments, the impurities in the final product are less than 20%, or less than 15%, or less than 10%, or less than 5%, or less than 4%, or less than 3%, or less than 2%, or less than 1%, or less than 0.5%, or less than 0.1%. In other embodiments, the impurities in the final product are less than about 20%, or less than about 15%, or less than about 10%, or less than about 5%, or less than about 4%, or less than about 3%, or less than about 2%, or less than about 1%, or less than about 0.5%, or less than about 0.1%. In other embodiments, the impurities consisting of tocols or tocol derivatives in the final product are less than 5%, less than 4%, less than 3%, less than 2%, less than 1%, less than 0.5% or less than 0.1%. In other embodiments, the impurities consisting of tocols or tocol derivatives in the final product are less than about 5%, less than about 4%, less than about 3%, less than about 2%, less than about 1%, less than about 0.5% or less than about 0.1%. In one embodiment, the invention provides a method for large-scale production, enrichment, and/or isolation of alpha-tocotrienol, such as quantities of material containing alpha-tocotrienol of at least 50 grams, at least 100 grams, at least 250 grams, at least 500 grams, at least 1 kilogram, at least 2 kilograms, at least 5 kilograms, or at least 10 kilograms, or at least about 50 grams, at least about 100 grams, at least about 250 grams, at least about 500 grams, at least about 1 kilogram, at least about 2 kilograms, at least about 5 kilograms, or at least about 10 kilograms. The quantity of material containing alpha-tocotrienol can have any purity level as recited herein.

In some of the above mentioned embodiments, the process involves an additional optional step, wherein the alpha-tocotrienol of high purity is oxidized to produce alpha-tocotrienol quinone of high purity. In one embodiment, the conversion of alpha-tocotrienol to alpha-tocotrienol quinone is carried out under buffered conditions. In one embodiment, the buffer and/or base employed during conversion of alpha-tocotrienol to alpha-tocotrienol quinone is sodium carbonate, sodium hydrogen carbonate, potassium carbonate, potassium hydrogen carbonate, phosphate buffer, or any mixture in any proportion of two or more of the foregoing buffers.

In any of the embodiments above, the processes of the invention can yield alpha-tocotrienol quinone of high purity. In some embodiments, the purity is in the range of 80% to 99.9%, or in the range of 85% to 99.9%, or in the range of 90% to 99.9%, or in the range of 95% to 99.9%. In some embodiments, the purity is in the range of about 80% to about 99.9%, or in the range of about 85% to about 99.9%, or in the range of about 90% to about 99.9%, or in the range of about 95% to about 99.9%. In some embodiments, the purity is more than 80%, or more than 85%, or more than 90%, or more than 91%, or more than 92%, or more than 93%, or more than 94%, or more than 95%, or more than 96%, or more than 97%, or more than 98%, or more than 99%, or more than 99.5%, or more than 99.9%. In some embodiments, the purity is more than about 80%, or more than about 85%, or more than about 90%, or more than about 91%, or more than about 92%, or more than about 93%, or more than about 94%, or more than about 95%, or more than about 96%, or more than about 97%, or more than about 98%, or more than about 99%, or more than about 99.5%, or more than about 99.9%. In other embodiments, the impurities in the final product are less than 20%, or less than 15%, or less than 10%, or less than 5%, or less than 4%, or less than 3%, or less than 2%, or less than 1%, or less than 0.5%, or less than 0.1%. In other embodiments, the impurities in the final product are less than about 20%, or less than about 15%, or less than about 10%, or less than about 5%, or less than about 4%, or less than about 3%, or less than about 2%, or less than about 1%, or less than about 0.5%, or less than about 0.1%. In other embodiments, the impurities consisting of tocols or tocol derivatives in the final product are less than 5%, less than 4%, less than 3%, less than 2%, less than 1%, less than 0.5% or less than 0.1%. In other embodiments, the impurities consisting of tocols or tocol derivatives in the final product are less than about 5%, less than about 4%, less than about 3%, less than about 2%, less than about 1%, less than about 0.5% or less than about 0.1%. In one embodiment, the invention provides a method for large-scale production, enrichment, and/or isolation of alpha-tocotrienol quinone, such as quantities of material containing alpha-tocotrienol quinone of at least 50 grams, at least 100 grams, at least 250 grams, at least 500 grams, at least 1 kilogram, at least 2 kilograms, at least 5 kilograms, or at least 10 kilograms, or at least about 50 grams, at least about 100 grams, at least about 250 grams, at least about 500 grams, at least about 1 kilogram, at least about 2 kilograms, at least about 5 kilograms, or at least about 10 kilograms. The quantity of material containing alpha-tocotrienol quinone can have any purity level as recited herein.

In another embodiment, the invention comprises a method for oxidizing alpha-tocotrienol to alpha-tocotrienol quinone with minimal isomerization of the double bonds of the triene moiety. In some embodiments, the alpha-tocotrienol quinone, 2-((6E,10E)-3R-hydroxy-3,7,11,15-tetramethylhexadeca-6,10,14-trienyl)-3,5,6-trimethylcyclohexa-2,5-diene-1,4-dione, produced by the method comprises at least about 80%, at least shoot 90%, at least about 95%, at least about 96%, at least about 97%, at least about 98%, at least about 99%, at least about 99.5%, or at least about 99.9% of the 2-(3-hydroxy-3,7,11,15-tetramethylhexadeca-6,10,14-trienyl)-3,5,6-trimethylcyclohexa-2,5-diene-1,4-dione material present.

In any of the above embodiments, the oxidation of alpha-tocotrienol to alpha-tocotrienol quinone can be performed with cerium (IV) ammonium nitrate.

In another embodiment, a solution of alpha-tocotrienol quinone, in a solvent such as isopropylacetate, n-heptane, or a mixture of isopropylacetate and n-heptane, is placed on a chromatography column packed with silica gel. The silica gel can contain between about 0.1-5% by weight of sodium hydrogen carbonate, such as about 0.5-2% by weight or about 1% by weight of sodium hydrogen carbonate. The alpha-tocotrienol quinone can be eluted from the silica gel/NaHCO$_3$ with solvents, such as n-heptane, isopropylacetate, or n-heptane:isopropylacetate in ratios of about 100:1, about 100:5, about 100:10, or about 100:15. The recovered solution of alpha-tocotrienol quinone can be concentrated to give alpha-tocotrienol quinone of high purity.

In another embodiment, the foregoing quantities of alpha-tocotrienol or alpha-tocotrienol quinone can be produced using a single performance of the method, that is, with a single iteration of the steps of the method.

In some embodiments, as described in FIG. 3, the process comprises the steps of:

3a.) reacting a plant extract mixture, comprising at least one non-alpha tocotrienol, with suitable reagents which will react with the one or more non-alpha-tocols to introduce a functional group in the free 5 and/or 7 positions of the one or more non-alpha-tocols;

3b.) separating the one or more non-alpha-tocol homologues that have been functionalized, from the alpha-tocotrienol, the optional alpha tocopherol and other non-tocol compounds that may be present;

3c.) optionally further separating the alpha-tocotrienol in the mixture separated in step (3b), from the optional alpha tocopherol and other non-tocol compounds;

3d.) chemically reacting the one or more non-alpha-tocol functionalized homologues to give alpha-tocotrienol;

3e.) optionally combining the alpha-tocotrienol from step (3c) with the newly produced alpha-tocotrienol from step (3d) to give alpha-tocotrienol of high purity; and 3f.) oxidizing the alpha-tocotrienol from step (3e) to give alpha-tocotrienol quinone of high purity.

In another embodiment, step 3b) is followed by an optional step 3b1) of filtering a solution of the one or more non-alpha-tocols homologues that have been functionalized. Filtration can be performed using diatomaceous earth such as Celite® or any other method of filtration known to the skilled artisan.

In another embodiment, step 3d) is followed by an optional step 3d1), and/or step 3e) is followed by an optional step 3e1), wherein a solution of the alpha-tocotrienol (in a solvent such as toluene) produced by the reduction is mixed with silica gel. The silica gel is removed by filtration, and the remaining filtrate is concentrated to give alpha-tocotrienol of high purity.

In another embodiment, both steps 3b1) and 3d1), both steps 3b1) and 3e1), or all three steps 3b1), 3d1), and 3e1) are performed.

In one embodiment, introduction of a functional group in the free 5 and/or 7 positions of the non-alpha tocol homologues comprises introduction of a group which provides for increased differential solubility of the functionalized non-alpha tocol homologues compared to non-functionalized compounds in the starting material, source material, or extract. The increased differential solubility can be differential solubility in a single solvent, or increased differential solubility between two or more solvents in a mixed solvent system. In one embodiment, the introduction of a functional group in the free 5 and/or 7 positions of the non-alpha tocol homologues is accomplished without reducing the double bonds present in tocotrienol compounds and/or without causing isomerization of the double bonds present in tocotrienol compounds. In one embodiment, the step of chemically reacting the non-alpha tocol functionalized homologues to produce alpha-tocotrienol is accomplished without reducing the double bonds present in tocotrienol compounds and/or without causing isomerization of the double bonds present in tocotrienol compounds.

In one embodiment, the functionalization is introduced by amino-alkylation followed by acidification, thus converting the non-alpha-tocotrienol into the corresponding amino-alkylated product and converting said products to acid salts. In some embodiments, the functionalization is introduced by amino-alkylation with a formaldehyde equivalent, such as paraformaldehyde, and an amine, such as a secondary amine, such as a cyclic amine such as 1-methylpiperazine, piperidine or morpholine. In some embodiments, the functionalization is introduced by amino-alkylation with paraformaldehyde and 1-methylpiperazine. In some embodiments, the functionalization is introduced by amino-alkylation with paraformaldehyde and morpholine.

In any of the embodiments above, the processes of the invention can yield alpha-tocotrienol of high purity. In some embodiments, the purity is in the range of 80% to 99.9%, or in the range of 85% to 99.9%, or in the range of 90% to 99.9%, or in the range of 95% to 99.9%. In some embodiments, the purity is in the range of about 80% to about 99.9%, or in the range of about 85% to about 99.9%, or in the range of about 90% to about 99.9%, or in the range of about 95% to about 99.9%. In some embodiments, the purity is more than 80%, or more than 85%, or more than 90%, or more than 91%, or more than 92%, or more than 93%, or more than 94%, or more than 95%, or more than 96%, or more than 97%, or more than 98%, or more than 99%, or more than 99.5%, or more than 99.9%. In some embodiments, the purity is more than about 80%, or more than about 85%, or more than about 90%, or more than about 91%, or more than about 92%, or more than about 93%, or more than about 94%, or more than about 95%, or more than about 96%, or more than about 97%, or more than about 98%, or more than about 99%, or more than about 99.5%, or more than about 99.9%. In other embodiments, the impurities in the final product are less than 20%, or less than 15%, or less than 10%, or less than 5%, or less than 4%, or less than 3%, or less than 2%, or less than 1%, or less than 0.5%, or less than 0.1%. In other embodiments, the impurities in the final product are less than about 20%, or less than about 15%, or less than about 10%, or less than about 5%, or less than about 4%, or less than about 3%, or less than about 2%, or less than about 1%, or less than about 0.5%, or less than about 0.1%. In other embodiments, the impurities consisting of tocols or tocol derivatives in the final product are less than 5%, less than 4%, less than 3%, less than 2%, less than 1%, less than 0.5% or less than 0.1%. In other embodiments, the impurities consisting of tocols or tocol derivatives in the final product are less than about 5%, less than about 4%, less than about 3%, less than about 2%, less than about 1%, less than about 0.5% or less than about 0.1%. In one embodiment, the invention provides a method for large-scale production, enrichment, and/or isolation of alpha-tocotrienol, such as quantities of material containing alpha-tocotrienol of at least 50 grams, at least 100 grams, at least 250 grams, at least 500 grams, at least 1 kilogram, at least 2 kilograms, at least 5 kilograms, or at least 10 kilograms, or at least about 50 grams, at least about 100 grams, at least about 250 grams, at least about 500 grams, at least about 1 kilogram, at least about 2 kilograms, at least about 5 kilograms, or at least about 10 kilograms. The quantity of material containing alpha-tocotrienol can have any purity level as recited herein.

In any of the embodiments above, the processes of the invention can yield alpha-tocotrienol quinone of high purity. In some embodiments, the purity is in the range of 80% to 99.9%, or in the range of 85% to 99.9%, or in the range of 90% to 99.9%, or in the range of 95% to 99.9%. In some embodiments, the purity is in the range of about 80% to about 99.9%, or in the range of about 85% to about 99.9%, or in the range of about 90% to about 99.9%, or in the range of about 95% to about 99.9%. In some embodiments, the purity is more than 80%, or more than 83%, or more than 90%, or more than 91%, or more than 92%, or more than 93%, or more than 94%, or more than 95%, or more than 96%, or more than 97%, or more than 98%, or more than 99%, or more than 99.5%, or more than 99.9%. In some embodiments, the purity is more than about 80%, or more than about 85%, or more than about 90%, or more than about 91%, or more than about 92%, or more than about 93%, or more than about 94%, or more than about 95%, or more than about 96%, or more than about 97%, or more than about 98%, or more than about 99%, or more than about 99.5%, or more than about 99.9%. In other embodiments, the impurities in the final product are less than 20%, or less than 15%, or less than 10%, or less than 5%, or less than 4%, or less than 3%, or less than 2%, or less than 1%, or less than 0.5%, or less than 0.1%. In other embodiments, the impurities in the final product are less than about 20%, or less than about 15%, or less than about 10%, or less than about 5%, or less than about 4%, or less than about 3%, or less than about 2%, or less than about 1%, or less than about 0.5%, or less than about 0.1%. In other embodiments, the impurities consisting of tocols or tocol derivatives in the final product are less than 5%, less than 4%, less than 3%, less than 2%, less than 1%, less than 0.5% or less than 0.1%. In other embodiments, the impurities consisting of tocols or tocol derivatives in the final product are less than about 5%, less than about 4%, less than about 3%, less than about 2%, less than about 1%, less than about 0.5% or less than about 0.1%. In one embodiment, the invention provides a method for large-scale production, enrichment, and/or isolation of alpha-tocotrienol quinone, such as quantities of material containing alpha-tocotrienol quinone of at least 50 grams, at least 100 grams, at least 250 grams, at least 500 grams, at least 1 kilogram, at least 2 kilograms, at least 5 kilograms, or at least 10 kilograms, or at least about 50 grams, at least about 100 grams, at least about 250 grams, at least about 500 grams, at least about 1 kilogram, at least about 2 kilograms, at least about 5 kilograms, or at least about 10 kilograms. The quantity of material containing alpha-tocotrienol quinone can have any purity level as recited herein.

In one embodiment, the conversion of alpha-tocotrienol to alpha-tocotrienol quinone of step 3f) is carried out under buffered conditions. In one embodiment, the buffer and/or base employed during conversion of alpha-tocotrienol to alpha-tocotrienol quinone of step 3f) is sodium carbonate, sodium hydrogen carbonate, potassium carbonate, potassium hydrogen carbonate, phosphate buffer, or any mixture in any proportion of two or more of the foregoing buffers.

In another embodiment, the invention comprises a method for oxidizing alpha-tocotrienol to alpha-tocotrienol quinone with minimal isomerization of the double bonds of the triene moiety. In some embodiments, the alpha-tocotrienol quinone, 2-((6E,10E)-3R-hydroxy-3,7,11,15-tetramethylhexadeca-6,10,14-trienyl)-3,5,6-trimethylcyclohexa-2,5-diene-1,4-dione, produced by the method comprises at least about 80%, at least about 90%, at least about 95%, at least about 96%, at least about 97%, at least about 98%, at least about 99%, at least about 99.5%, or at least about 99.9% of the 2-(3-hydroxy-3,7,11,15-tetramethylhexadeca-6,10,14-trienyl)-3,5,6-trimethylcyclohexa-2,5-diene-1,4-dione material present.

In any of the above embodiments, the oxidation of alpha-tocotrienol to alpha-tocotrienol quinone can be performed with cerium (IV) ammonium nitrate.

In another embodiment, a solution of alpha-tocotrienol quinone, in a solvent such as isopropylacetate, n-heptane, or a mixture of isopropylacetate and n-heptane, is placed on a chromatography column packed with silica gel. The silica gel can contain between about 0.1-5% by weight of sodium hydrogen carbonate, such as about 0.5-2% by weight or about 1% by weight of sodium hydrogen carbonate. The alpha-tocotrienol quinone can be eluted from the silica gel/NaHCO$_3$ with solvents, such as n-heptane, isopropylacetate, or n-heptane:isopropylacetate in ratios of about 100:1, about 100:5, about 100:10, or about 100:15. The recovered solution of alpha-tocotrienol quinone can be concentrated to give alpha-tocotrienol quinone of high purity.

In another embodiment, the foregoing quantities of alpha-tocotrienol or alpha-tocotrienol quinone can be produced using a single performance of the method, that is, with a single iteration of the steps of the method.

In some embodiments, as described in FIG. 4, the process comprises the steps of:

4a.) reacting a palm oil extract mixture, comprising at least one non-alpha tocotrienol, with amino-alkylating agents which will react with the one or more non-alpha-tocols to introduce a functional group in the free 5 and/or 7 positions of the one or more non-alpha-tocotrienols and converting the products into acid salts;

4b.) separating the one or more non-alpha-tocotrienol acid salts of the products (from step 4a) from the alpha-tocotrienol, optional alpha tocopherol and other non-tocol compounds that may be present;

4c.) reducing the one or more non-alpha-tocotrienol functionalized homologues (from step 4b) with a reducing agent to give alpha-tocotrienol of high purity; and 4d.) oxidizing the alpha-tocotrienol from step (4c) to give alpha-tocotrienol quinone of high purity.

In another embodiment, step 4b) is followed by an optional step 4b1) of filtering a solution of the one or more non-alpha-tocols homologues that have been functionalized. Filtration can be performed using diatomaceous earth such as Celite® or any other method of filtration known to the skilled artisan.

In another embodiment, step 4c) is followed by an optional step 4c1), wherein a solution of the alpha-tocotrienol (in a solvent such as toluene) produced by the reduction is mixed with silica gel. The silica gel is removed by filtration, and the remaining filtrate is concentrated to give alpha-tocotrienol of high purity.

In another embodiment, both steps 4b1) and 4c1) are performed.

In one embodiment, the conversion of alpha-tocotrienol to alpha-tocotrienol quinone of step 4d) is carried out under buffered conditions. In one embodiment, the buffer and/or base employed during conversion of alpha-tocotrienol to alpha-tocotrienol quinone of step 4d) is sodium carbonate, sodium hydrogen carbonate, potassium carbonate, potassium hydrogen carbonate, phosphate buffer, or any mixture in any proportion of two or more of the foregoing buffers.

In one embodiment, introduction of an aminoalkyl group in the free 5 and/or 7 positions of the non-alpha tocol homologues provides for increased differential solubility of the functionalized non-alpha tocol homologues compared to non-functionalized compounds in the starting material, source material, or extract. The increased differential solubility can be differential solubility in a single solvent, or increased differential solubility between two or more solvents in a mixed solvent system. In one embodiment, the introduction of an aminoalkyl group in the free 5 and/or 7 positions of the non-alpha tocol homologues is accomplished without reducing the double bonds present in tocotrienol compounds and/or without causing isomerization of the double bonds present in tocotrienol compounds. In one embodiment, the step of reducing the non-alpha tocol functionalized homologues to produce alpha-tocotrienol is accomplished without reducing the double bonds present in tocotrienol compounds and/or without causing isomerization of the double bonds present in tocotrienol compounds.

In another embodiment, the amino-alkylation is performed with a formaldehyde equivalent, such as paraformaldehyde, and an amine, such as a secondary amine, such as a cyclic amine selected from 1-methylpiperazine, piperidine or morpholine. In yet another embodiment the amino-alkylation is performed with paraformaldehyde and 1-methylpiperazine. In yet another embodiment, the amino-alkylation is performed with paraformaldehyde and morpholine.

In another embodiment, a solution of alpha-tocotrienol quinone, in a solvent such as isopropylacetate, n-heptane, or a mixture of isopropylacetate and n-heptane, is placed on a chromatography column packed with silica gel. The silica gel can contain between about 0.1-5% by weight of sodium hydrogen carbonate, such as about 0.5-2% by weight or about 1% by weight of sodium hydrogen carbonate. The alpha-tocotrienol quinone can be eluted from the silica gel/NaHCO$_3$ with solvents, such as n-heptane, isopropylacetate, or n-heptane:isopropylacetate in ratios of about 100:1, about 100:5, about 100:10, or about 100:15. The recovered solution of alpha-tocotrienol quinone can be concentrated to give alpha-tocotrienol quinone of high purity.

In any of the embodiments above, the processes of the invention can yield alpha-tocotrienol of high purity. In some embodiments, the purity is in the range of 80% to 99.9%, or in the range of 85% to 99.9%, or in the range of 90% to 99.9%, or in the range of 95% to 99.9%. In some embodiments, the purity is in the range of about 80% to about 99.9%, or in the range of about 85% to about 99.9%, or in the range of about 90% to about 99.9%, or in the range of about 95% to about 99.9%. In some embodiments, the purity is more than 80%, or more than 85%, or more than 90%, or more than 91%, or more than 92%, or more than 93%, or more than 94%, or more than 95%, or more than 96%, or more than 97%, or more than 98%, or more than 99%, or more than 99.5%, or more than 99.9%. In some embodiments, the purity is more than about 80%, or more than about 85%, or more than about 90%, or more than about 91%, or more than about 92%, or more than about 93%, or more than about 94%, or more than about 95%, or more than about 96%, or more than about 97%, or more than about 98%, or more than about 99%, or more than about 99.5%, or more than about 99.9%. In other embodiments, the impurities in the final product are less than 20%, or less than 15%, or less than 10%, or less than 5% or less than 4%, or less than 3%, or less than 2%, or less than 1%, or less than 0.5%, or less than 0.1%. In other embodiments, the impurities in the final product are less than about 20%, or less than about 15%, or less than about 10%, or less than about 5%, or less than about 4%, or less than about 3%, or less than about 2%, or less than about 1%, or less than about 0.5%, or less than about 0.1%. In other embodiments, the impurities consisting of tocols or tocol derivatives in the final product are less than 5%, less than 4%, less than 3%, less than 2%, less than 1%, less than 0.5% or less than 0.1%. In other embodiments, the impurities consisting of tocols or tocol derivatives in the final product are less than about 5%, less than about 4%, less than about 3%, less than about 2%, less than about 1%, less than about 0.5% or less than about 0.1%. In one embodiment, the invention provides a method for large-scale production, enrichment, and/or isolation of alpha-tocotrienol, such as quantities of material containing alpha-tocotrienol of at least 50 grams, at least 100 grams, at least 250 grams, at least 500 grams, at least 1 kilogram, at least 2 kilograms, at least 3 kilograms, or at least 10 kilograms, or at least about 50 grams, at least about 100 grams, at least about 250 grams, at least about 500 grams, at least about 1 kilogram, at least about 2 kilograms, at least about 5 kilograms, or at least about 10 kilograms. The quantity of material containing alpha-tocotrienol can have any purity level as recited herein.

In any of the processes for the production of alpha-tocotrienol quinone described above, the alpha-tocotrienol quinone is of high purity. In some processes, the purity is in the range of 80% to 99%, or in the range of 85% to 99% or in the range of 90% to 99%, or in the range of 95% to 99%. In some processes, the purity is more than 80%, or more than 85%, more than 90%, or more than 91%, or more than 92%, or more than 93%, or more than 94%, or more than 95%, or more than 96%, or more than 97%, or more than 98%, or more than 99%, or more than 99.5%, or more than 99.9%. In other embodiments, the impurities in the final product are less than 20%, or less than 15%, or less than 10%, or less than 5%, or less than 4%, or less than 3%, or less than 2%, or less than 1%, or less than 0.5%, or less than 0.1%. In some embodiments, the impurities consisting of tocols or tocol derivatives in the final product are less than 5%, or less than 4%, or less than 3%, or less than 2%, or less than 1%, or less than 0.5%, or less than 0.1%. In some processes, the purity is in the range of about 80% to about 99%, or in the range of about 85% to about 99% or in the range of about 90% to about 99%, or in the range of about 95% to about 99%. In some processes, the purity is more than about 80%, or more than about 83%, more than about 90%, or more than about 91%, or more than about 92%, or more than about 93%, or more than about 94%, or more than about 95%, or more than about 96%, or more than about 97%, or more than about 98%, or more than about 99%, or more than about 99.5%, or more than about 99.9%. In other embodiments, the impurities in the final product are less than about 20%, or less than about 15%, or less than about 10%, or less than about 5%, or less than about 4%, or less than about 3%, or less than about 2%, or less than about 1%, or less than about 0.5%, or less than about 0.1%. In some embodiments, the impurities consisting of tocols or tocol derivatives in the final product are less than about 5%, or less than about 4%, or less than about 3%, or less than about 2%, or less than about 1%, or less than about 0.5%, or less than about 0.1%.

In another embodiment, the invention comprises a method for oxidizing alpha-tocotrienol to alpha-tocotrienol quinone with minimal isomerization of the double bonds of the triene moiety. In some embodiments, the alpha-tocotrienol quinone, 2-((6E,10E)-3R-hydroxy-3,7,11,15-tetramethylhexadeca-6,10,14-trienyl)-3,5,6-trimethylcyclohexa-2,5-diene-1,4-dione, produced by the method comprises at least about 80%, at least about 90%, at least about 95%, at least about 96%, at least about 97%, at least about 98%, at least about 99%, at least about 99.5%, or at least about 99.9% of the 2-(3-hydroxy-3,7,11,15-tetramethylhexadeca-6,10,14-trienyl)-3,5,6-trimethylcyclohexa-2,5-diene-1,4-dione material present.

In any of the embodiments recited above, the non-alpha tocols can be reacted with a formaldehyde equivalent and at least one amine compound of the formula H—N($R_{11}$)($R_{12}$), where $R_{11}$ and $R_{12}$ are independently selected from the group consisting of H and $C_1$-$C_8$ alkyl or where $R_{11}$ and $R_{12}$ are combined together with the nitrogen to which they are bonded to form a five-to-eight membered heterocyclic ring, said heterocyclic ring having zero, one, or two additional heteroatoms in addition to the nitrogen to which $R_{11}$ and $R_{12}$ are bonded.

In any of the above embodiments, the oxidation of alpha-tocotrienol to alpha-tocotrienol quinone can be performed with cerium (IV) ammonium nitrate.

In another embodiment, the quantities of alpha-tocotrienol or alpha-tocotrienol quinone described herein, at any level of purity described herein, can be produced using a single performance of a method recited herein, that is, with a single iteration of the steps of the method.

METHODS FOR CARRYING OUT THE INVENTION

Figure 1:
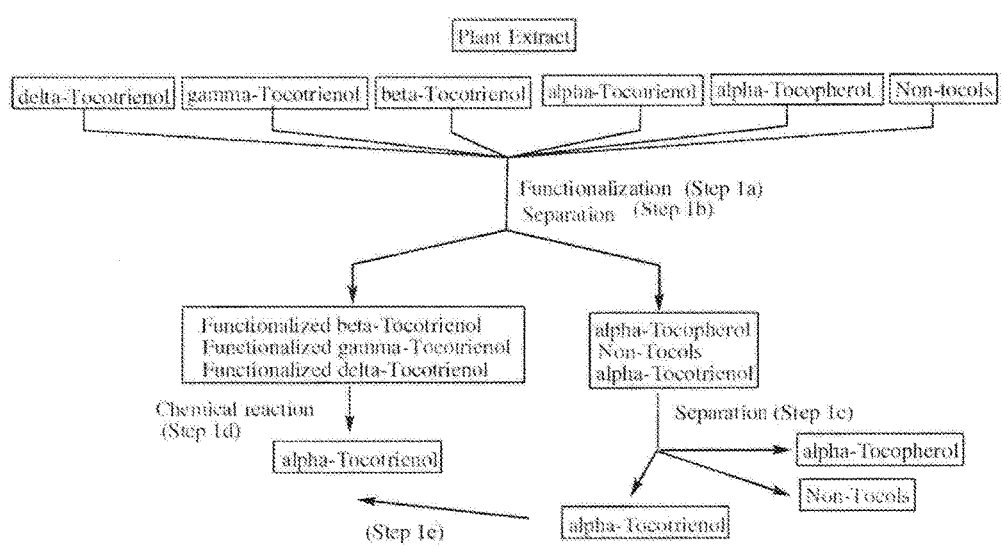
FIG. 1 is a flow chart depicting certain processes of the invention.
Figure 2:
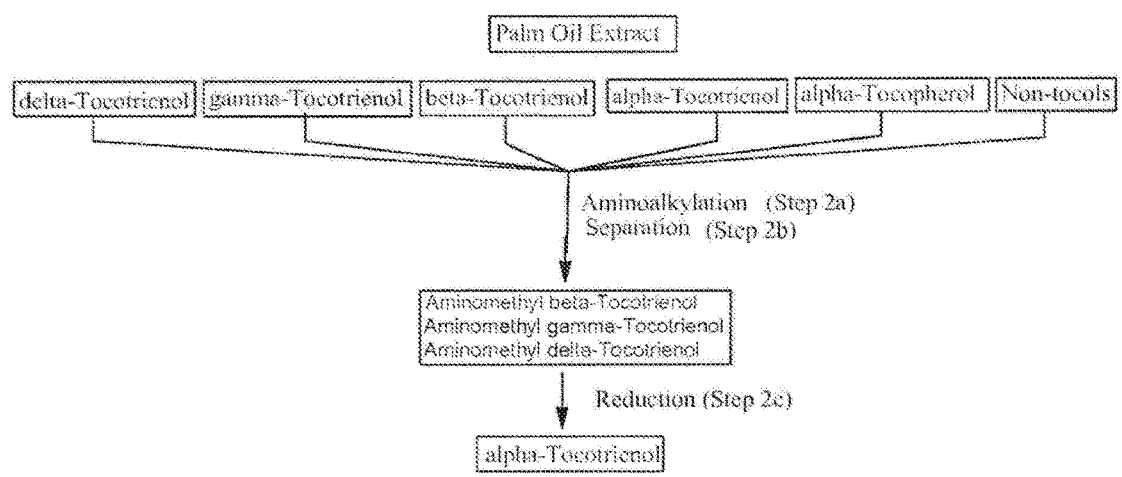
FIG. 2 is a flow chart depicting additional processes of the invention.
Figure 3:
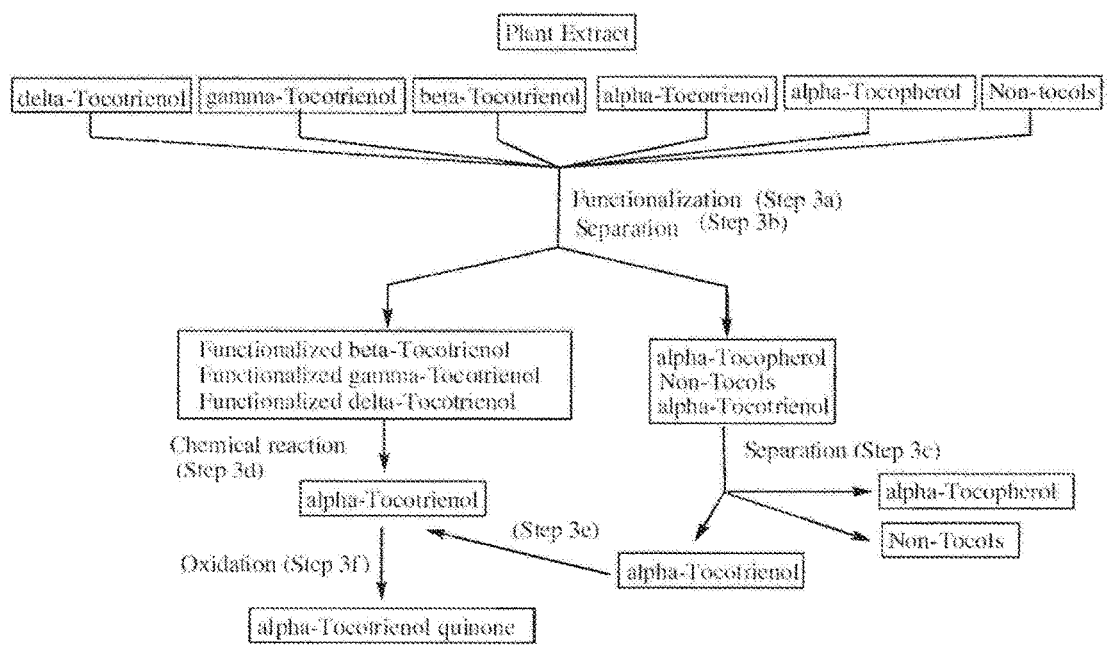
FIG. 3 is a flow chart depicting additional processes of the invention.
Figure 4:
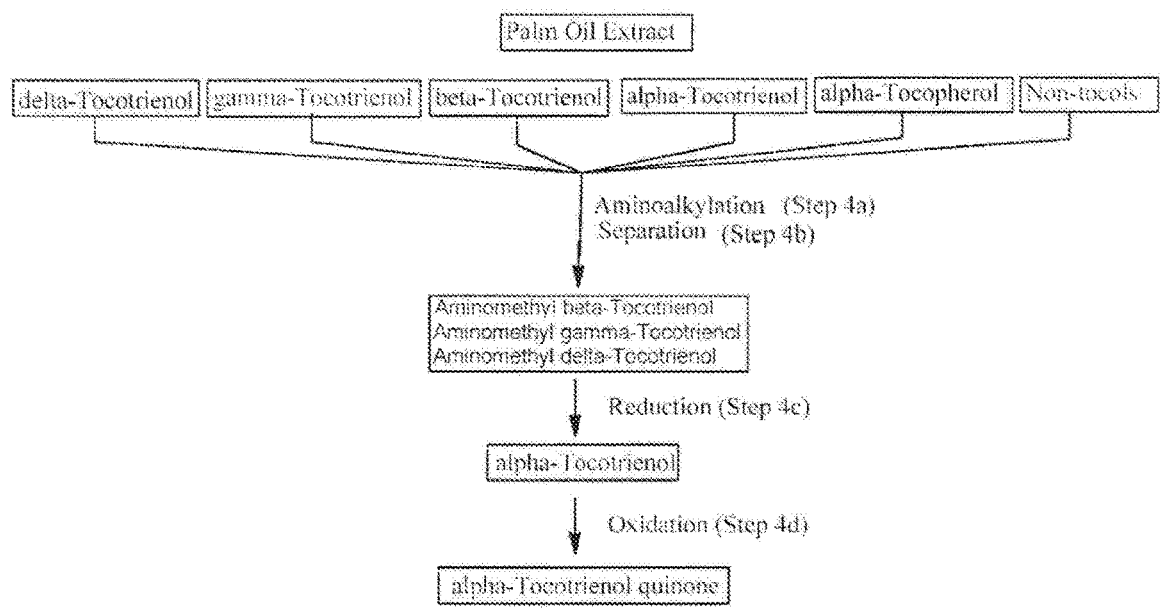
FIG. 4 is a flow chart depicting additional processes of the invention.

The invention embraces a method for production, enrichment and/or isolation of pure alpha-tocotrienol from natural extracts that comprise mixed tocotrienols.

The term "tocols" refers to tocopherols and tocotrienols as described herein.

The term "non-tocols" refers to phytonutrients or organic materials that may be present in the extract, but are not tocopherols or tocotrienols.

The term "amino-alkylation," also known as the Mannich reaction, is a reaction that effects amino-alkyl addition. The reaction can be conducted from at about room temperature up to about 140° C. for a sufficient length of time to effectuate amino-alkylation. The reagents necessary are a source of formaldehyde (a "formaldehyde equivalent") and an amine. Any primary or secondary amine, including amines such as cyclic and aromatic amines, alkyl amines, and polyamines, as well as ammonia, can be used. Particular examples of suitable amines are dibutyl amine, di-isopropyl amine, dimethyl amine, diethyl amine, dipropyl amine, 1-methylpiperazine, N,N,N'-trimethylethylenediamine, piperidine, pyrrolidine and morpholine. Sources of formaldehyde (i.e., formaldehyde equivalents) include, but are not limited to, paraformaldehyde, formaline, formaldehyde gas, trioxane and hexamethylenetetramine. The relative molar concentration of the formaldehyde equivalent and the amine are maintained in equimolar amounts, but the relative concentrations may be varied as long as there is at least one mole of amine and at least one mole of formaldehyde for every mole of free aromatic position on the tocotrienols, and, if present, any other compounds that will react with the formaldehyde and amine reagents. Either the amine or formaldehyde component may be present in an amount of from about 1 to about 20 moles per mole of free aromatic position on tocotrienol, and, if present, any other compounds that will react with the formaldehyde and amine reagents, particularly in a molar amount of at least about four times greater than the free aromatic positions on tocotrienol present, and, if present, any other compounds that will react with the formaldehyde and amine reagents. This process could also be accomplished step-wise, for example by formylation followed by reductive amination, or by pre-formation of the "Mannich" reagent—the alkyliminium or functional equivalent intermediate.

The starting material is a mixed tocotrienol extract that may also optionally comprise alpha tocopherol in amounts that may vary depending on the source of the extract. Naturally produced alpha-tocotrienol and optional alpha tocopherol are separated from the beta, gamma, and delta-tocotrienol homologues of alpha-tocotrienol, by reacting the mixture of tocotrienols and optional alpha tocopherol with an appropriate reagent or reagents to introduce a functional group at the free 5 and/or 7 positions of the non-alpha-tocotrienols. For example, the starting material can be amino-alkylated to introduce amino-alkylated groups on the beta, gamma, and delta-tocotrienols. As alpha-tocotrienol does not have a free ring position, any alpha-tocotrienol present in the mixture will not be amino-alkylated. The amino-alkylated groups will allow the separation of the amino-alkylated beta, gamma, and delta-tocotrienols from alpha-tocotrienol, alpha tocopherol and other non-tocol phytonutrients that may be present. The separation will be accomplished by partitioning between different organic solvents. Any non-polar organic solvents such as hexanes, heptanes, pentanes, petroleum ether, or mixtures thereof, can be used to take up the alpha tocopherol, alpha-tocotrienol and other phytonutrients or hydrocarbon impurities. The amino-alkylated products, optionally having been converted to an acid salt, can be partitioned in an acidic organic layer such as acetonitrile comprising formic acid. In another embodiment of the invention, the partitioning can be performed between an organic layer and an aqueous layer. Alternatively, the products from the amino-alkylation can be removed by first permethylating to the tetra alkyl ammonium salt, followed by reductive deamination under basic conditions (see for example Maeda, Y. et al., *JOC* (1994) 59, 7897-7901; and Tayama, E. et al, *Chem Letters* (2006) 35, 478-479).

By the term "reducing agent" is contemplated hydrides such as lithium aluminum hydride, sodium borohydride, and sodium cyano borohydride, borane complexes and electron donors such as sodium, lithium, magnesium, potassium, zinc, nickel, or amalgams thereof in the presence of a suitable proton source such as ammonium salts or carboxylic acids.

The phrase "impurities consisting of tocols or tocol derivatives in the final product" refers to beta-tocotrienol, gamma-tocotrienol, delta-tocotrienol, alpha-tocopherol, beta-tocopherol, gamma-tocopherol, or delta-tocopherol. Reference to "impurities" in the final product, without further specification, can refer to beta-tocotrienol, gamma-tocotrienol, delta-tocotrienol, alpha-tocopherol, beta-tocopherol, gamma-tocopherol, delta-tocopherol, and/or other non-tocol impurities. In one embodiment, solvents which can be readily removed by evaporation are not considered as impurities when determining the percentage of impurities present.

The quinone (cyclohexadienedione) form and dihydroquinone (benzenediol) form of the compounds disclosed herein are readily interconverted with appropriate reagents. The quinone can be treated in a biphasic mixture of an ethereal solvent with a basic aqueous solution of $Na_2S_2O_4$ (Vogel, A. I. et al. Vogel's Textbook of Practical Organic Chemistry, $5^{th}$ Edition, Prentice Hall: New York, 1996; Section 9.6.14 Quinones, "Reduction to the Hydroquinone"). Standard workup in the absence of oxygen yields the desired hydroquinone. The hydroquinone form can be oxidized to the quinone form with oxidizing agents such as ceric ammonium nitrate (CAN) or ferric chloride. The quinone and hydroquinone forms are also readily interconverted electrochemically, as is well known in the art. See, e.g., Section 33.4 of Streitweiser & Heathcock, Introduction to Organic Chemistry, New York: Macmillan, 1976.

Because reaction of alpha-tocopherol with cerium (IV) ammonium nitrate generates nitric acid, the oxidation can be carried out under buffered conditions. This can be accomplished by including sodium carbonate, sodium hydrogen carbonate, other carbonates such as potassium carbonate or potassium hydrogen carbonate, phosphate buffers, other buffers, or matures of any two or more of the foregoing buffers in any proportion, during the oxidation. Removal of acid during oxidation reduces isomerization of the double bonds in the triene moiety of the tocotrienol and tocotrienol quinone. Buffered conditions can also be maintained during workup of the alpha-tocotrienol quinone, for example, by mixing a percentage of a solid buffer such as sodium hydrogen carbonate with silica gel prior to placing the alpha-tocotrienol on the silica gel for elution.

When silica gel is used in the workup, the grade of silica gel used can be that used for standard preparative flash chromatography. For example, silica gel of about 60 Å pore size with a particle distribution of about 40 to 63 microns can be used. It can be used as is from the supplier, without further activation, or can be activated by heating in air or an oxygen-containing atmosphere.

This invention is further illustrated by the following example of a preferred embodiment thereof. This example is included merely for purposes of illustration and is not intended to limit the scope of the invention.

EXAMPLE

Step 1

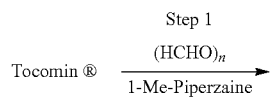

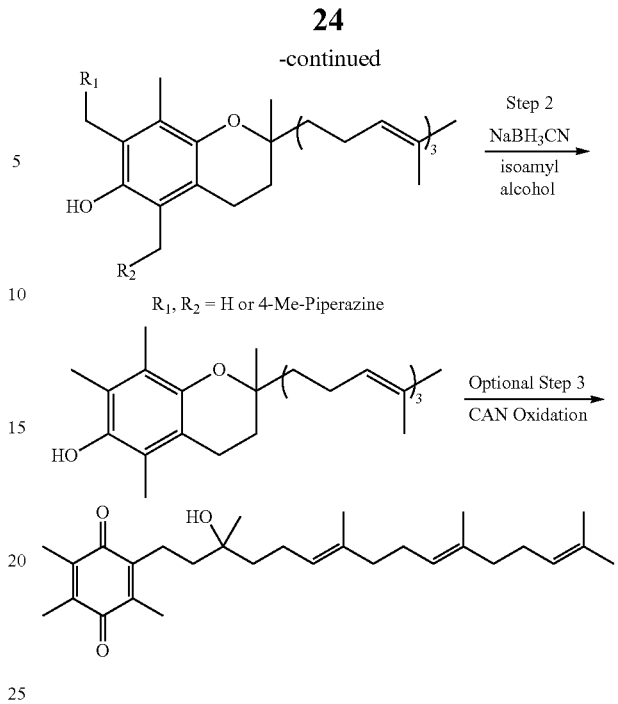

$R_1, R_2$ = H or 4-Me-Piperazine

General Procedures

All solvents and reagents were used as obtained from their respective suppliers except as noted. $^1H$ and $^{13}C$ NMR were obtained on a Varian Ultrashielded magnet at 400 MHz and 100 MHz respectively in deuterated solvents as noted. All spectra are referenced in ppm to either their residual solvent peak, as defined in Gottlieb, H. E. et al.; J. Org. Chem. 1997, 62, 7512-7515, or TMS at 0.00 ppm.

EXPERIMENTALS

Step 1-Aminomethylation

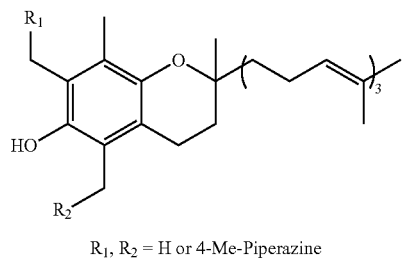

$R_1, R_2$ = H or 4-Me-Piperazine

To Tocomin™-50 (1.0 wt,) was added paraformaldehyde (0.08 wt, 95%) and 1-Methylpiperazine (0.3 vol). Use suspension was stirred at room temperature for 30 min, and then at 75° C. for 2 to 3 h. The solution was heated at 125° C. and monitored for conversion of starting material components to product components. The mixture was cooled to 30 to 40° C., diluted with acetonitrile (3.5 mL/g) and heptane (3.5 mL/g), and then cooled to 5° C., and treated dropwise with formic acid (1.0 vol). The bottom acetonitrile layer was separated and extracted with heptane (2×3.5 mL/g). The acetonitrile layer was diluted with tert-butyl methyl ether (3 mL/g) and cooled to 0° C. 45% w/w aqueous tribasic potassium phosphate solution (7 mL/g) was added dropwise (exothermic) so as to keep the temperature below 20° C. The organic layer was separated at room temperature, washed with saturated aqueous sodium chloride solution (23.1% w/w; 3 mL/g), and solvents were removed by distillation at up to 50° C. under vacuum. To the concentrated solution was added toluene (5 mL/g). Solvent (5 mL/g) was removed by distillation at up to 50° C. under vacuum. To the solution was added additional toluene (5 mL/g). Solvent (5 mL/g) was removed by distillation at up to 50° C. under vacuum. The residue was diluted with toluene (1.5 mL/g) and filtered through a pad of Celite™ packed from a suspension in toluene. The Celite™ cake was washed with toluene (1 mL/g). All filtrates were combined. The reaction mass yield was determined by loss-on-drying analysis of an aliquot of the reaction mixture. The solvents were removed by distillation at up to 50° C. under vacuum. The concentrated solution of product aminomethylated tocols was used, as is, in Step 2.

Step 2-Reduction

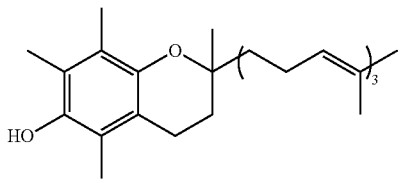

Note: unless otherwise indicated, all relative weight (wt) and volume (mL/g) equivalents in Step 2 are with respect to the loss on drying figure determined at the end of Stage 1.

To the residue prepared in Step 1 was added toluene (8 vol). A solvent exchange to a solution in 3-methylbutanol (3.0 vol) was then prepared by distillation at up to 50° C. under vacuum, with additions of 3-methylbutanol.

To sodium cyanoborohydride (0.43 wt) was added 3-methylbutanol (2 vol) at room temperature. The suspension was stirred at room temperature for 30 min, and then heated to 125° C. To this preheated mixture was added over 1.5 h the previously prepared solution of aminomethylated tocols in 3-methylbutanol (3.0 vol) followed by an additional rinse of 3-methylbutanol (0.5 vol). The mixture was heated at 125° C. and monitored for conversion of starting material components to product components.

The mixture was cooled to 50° C., diluted with heptane (5 vol), then cooled to 0° C., and treated with 45% w/w aqueous tribasic potassium phosphate solution (5.0 vol) (exothermic, gas evolution) so as to maintain a temperature below 25° C. The two-phase mixture was stirred at room temperature for 2 h, the organic layer was separated, washed with 45% w/w aqueous tribasic potassium phosphate solution (3 vol), and concentrated by distillation at up to 50° C. under vacuum. To the residue was added toluene (7 vol). The resulting solution was added to a mixture of silica gel (2 wt) and toluene (5.5 vol) with an additional rinse of toluene (2 vol). The silica gel suspension was stirred at room temperature for 1 h. The silica gel was removed by filtration and washed with toluene (2×5 vol). The combined filtrates were concentrated by distillation at up to 50° C. under vacuum. The residue solution was cooled to 30° C. and transferred to a rotoevaporator with toluene (2×1.4 vol) and further evaporated to dryness by distillation at up to 60° C. under vacuum to give alpha-tocotrienol. $^1$H-NMR (400 MHz, CDCl$_3$)=5.17-5.05 (m, 3H), 4.16 (s, 1H), 2.61 (t, J=6.8 Hz, 2H), 2.16-2.01 (m, 6H), 2.16 (s, 3H), 2.12 (s, 3H), 2.11 (s, 3H), 2.01-1.93 (m, 4H), 1.87-1.73 (m, 2H), 1.68-1.49 (m, 2H), 1.68 (s, 3H), 1.60 (s, 6H), 1.58 (s, 3H), 1.25 (s, 3H).

Step 3-Chroman to Quinone Oxidation

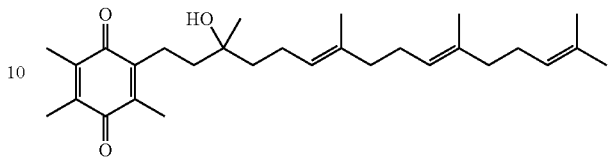

Note: unless otherwise indicated all relative weight (wt) and volume (mL/g) equivalents in Step 3 are with respect to the mass of this stage's starting material, the product of Step 2—alpha-tocotrienol.

The residue of Step 2 was dissolved in isopropyl acetate (10 vol), water (0.5 vol) was added, and the mixture was cooled to 0° C. A solution of cerium (IV) ammonium nitrate (2.74 wt) in water (3 vol) was prepared at room temperature and buffered by addition of saturated aqueous sodium carbonate solution (17.4% w/w; 0.75 vol). The buffered cerium (IV) ammonium nitrate solution was added over 30 min to the prepared mixture of alpha-tocotrienol from step 2 in isopropylacetate and water while maintaining the temperature at 0° C. The mixture was stirred at 0° C. and monitored for conversion of starting material components to product components. The organic layer was separated and treated for 2 h with a slurry of solid sodium hydrogen carbonate (2 wt) and solid sodium sulfate (2 wt) in isopropylacetate (5 vol). The suspension was filtered, the solids washed with isopropylacetate (1.5 vol), and the combined filtrates treated with sodium hydrogen carbonate (2×0.05 wt). The suspension was concentrated to a maximum extent while maintaining an agitable mixture by distillation at up to 45° C. under vacuum. The residue was cooled to 30° C. and diluted with n-heptane (10 vol). A chromatography column of silica gel (5 wt) and sodium hydrogen carbonate (0.05 wt) was prepared from a slurry in n-heptane. The mixture was eluted on the chromatography column and further eluted with mixtures of n-heptane/isopropylacetate in relative volume-ratios of 100:5 and then 100:10. Fractions were collected, treated with solid sodium hydrogen carbonate (ca. 0.1 to 1 g/L eluent), and analyzed for product content and purity. Acceptable fractions were combined, treated with additional solid sodium hydrogen carbonate (0.05 wt), and concentrated to a maximum extent while maintaining an agitable mixture by distillation of solvent at up to 45° C. under vacuum. Isopropylacetate (1 to 3 vol) was added and the mixture passed through a 0.45 to 1 um filter. The filtrate was evaporated to dryness by distillation of solvent at up to 40° C. under vacuum to give the product, alpha-tocotrienol quinone. $^1$H-NMR (400 MHz, C$_6$D$_6$) 5.37-5.28 (t br m, J=7 Hz, 2H), 5.28-5.20 (t br m, J=6 Hz, 1H), 2.53-2.46 (m, 2H), 2.25-2.15 (m, 6H), 2.15-2.07 (m, 4H) 1.91 (s, 3H), 1.73-1.71 (br d, J=1 Hz, 3H), 1.71-1.70 (br d, J=1 Hz, 3H, 1.68 (s, 6H), 1.62 (s, 3H), 1.57 (s, 3H), 1.54-1.47 (m, 2H), 1.47-1.40 (ddd, J=8.6, 1 Hz, 2H), 1.10 (s, 3H), 1.00 (s, 1H).

The disclosures of all publications, patents, patent applications and published patent applications referred to herein by an identifying citation are hereby incorporated herein by reference in their entirety.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A process for the production, enrichment and/or isolation of alpha-tocotrienol from a plant extract that comprises at least one non-alpha tocotrienol and that optionally comprises alpha-tocotrienol, optionally comprises alpha-tocopherol and optionally comprises other tocols, non-tocols and/or organic impurities, comprising the steps of:
   1a.) reacting the plant extract with suitable reagents which react with the one or more non-alpha-tocols to introduce a functional group in the free 5 and/or 7 position of the one or more non-alpha-tocols;
   1b.) separating the one or more non-alpha-tocols that have been functionalized in step (1a) from the optional alpha-tocotrienol and optional alpha tocopherol and optional non-tocol compounds that may be present;
   1c.) optionally further separating the alpha-tocotrienol in the mixture separated in step (1b), from the optional alpha tocopherol and from optional non-tocols;
   1d.) chemically reacting the separated one or more non-alpha-tocols that have been functionalized from step (1b) to give alpha-tocotrienol; and
   1e.) optionally combining the alpha-tocotrienol from step (1c) with the alpha-tocotrienol from step (1d) to give alpha-tocotrienol,
   wherein step 1a.) comprises amino-alkylation performed with a formaldehyde equivalent and 1-methylpiperazine, followed by acidification;
   and wherein step 1d.) comprises reduction performed with sodium cyano borohydride.

2. The process of claim 1, wherein the plant extract is selected from the group consisting of a palm oil extract, a palm fruit extract, a rice extract, a rice bran extract, a barley extract, an annatto extract, and a mixture thereof.

3. The process of claim 2, wherein the plant extract is a palm oil extract.

4. The process of claim 2, wherein the plant extract is Tocomin®.

5. The process of claim 1, additionally comprising an additional last step wherein the alpha-tocotrienol (from steps 1d and/or 1e) is oxidized to alpha-tocotrienol quinone.

6. The process of claim 3, additionally comprising an additional last step wherein the alpha-tocotrienol (from steps 1d and/or 1e) is oxidized to alpha-tocotrienol quinone.

7. The process of claim 1, additionally comprising a step 1b1) after step 1b), wherein a solution of the non-alpha-tocols that have been functionalized is filtered.

8. The process of claim 1, additionally comprising a step 1d1) after step 1d) wherein a solution of the alpha-tocotrienol produced in step 1d) is mixed with silica gel, followed by removal of the silica gel by filtration.

9. The process of claim 1, where the formaldehyde equivalent is paraformaldehyde.

10. The process of claim 1, wherein step 1d) is performed in the presence of 3-methylbutanol solvent.

11. The process of claim 1, wherein the formaldehyde equivalent is paraformaldehyde, and wherein step 1d) is performed in the presence of 3-methylbutanol solvent.

12. A compound selected from the group consisting of:

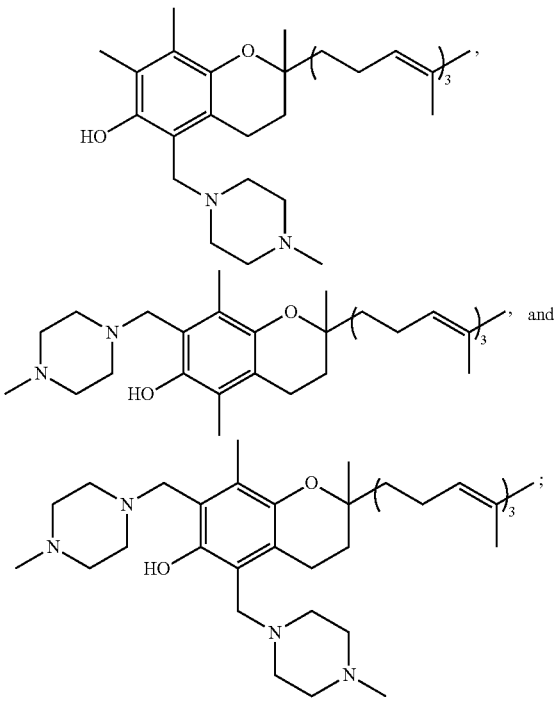

or an acid salt thereof; or a tetra alkyl ammonium salt thereof.

13. The compound of claim 12, wherein the compound is selected from the group consisting of:

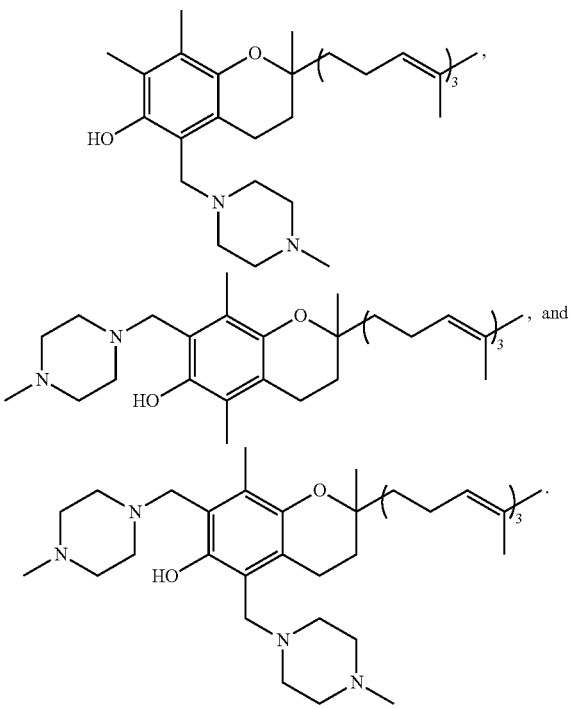

14. The compound of claim 12, wherein the compound is an acid salt thereof.

15. The compound of claim 14, wherein the acid salt is a formic acid salt.

16. The compound of claim 12, wherein the compound is a tetra-alkyl ammonium salt thereof.

* * * * *